US007257237B1

(12) United States Patent
Luck et al.

(10) Patent No.: US 7,257,237 B1
(45) Date of Patent: Aug. 14, 2007

(54) REAL TIME MARKERLESS MOTION TRACKING USING LINKED KINEMATIC CHAINS

(75) Inventors: Jason P. Luck, Arvada, CO (US); Daniel E. Small, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 702 days.

(21) Appl. No.: 10/794,331

(22) Filed: Mar. 4, 2004

Related U.S. Application Data

(60) Provisional application No. 60/452,773, filed on Mar. 7, 2003.

(51) Int. Cl.
*G06T 17/10* (2006.01)
*G06T 7/20* (2006.01)
*G06K 9/32* (2006.01)
*G06K 9/64* (2006.01)

(52) U.S. Cl. .................................. 382/103; 382/154
(58) Field of Classification Search ................ 348/169; 382/103, 154
See application file for complete search history.

(56) References Cited

U.S. PATENT DOCUMENTS

| | | | |
|---|---|---|---|
| 5,930,379 A * | 7/1999 | Rehg et al. ................. | 382/107 |
| 6,240,198 B1 * | 5/2001 | Rehg et al. ................. | 382/103 |
| 6,492,986 B1 | 12/2002 | Metaxas et al. | |
| 6,574,353 B1 | 6/2003 | Schoepfin et al. | |

OTHER PUBLICATIONS

Cheung et al. Jun. 2000. A Real Time System for Robust 3d Voxel Reconstruction of Human Motions. Proceedings of the IEEE Conference of Computer Vision and Pattern Recognition, Hilton Head, SC.*

Kakadiaris et al. Jun. 1996. Model-Based Estimation of 3D Human Motion with Occlusion Based on Active Multi-Viewpoint Selection. Proceedings of the IEEE Conference of Computer Vision and Pattern Recognition, San Francisco, CA.*

Kakadiaris et al. Jun. 1995. 3D human body model acquisition from multiple views. Proceedings of the IEEE Conference of Computer Vision, Cambridge, MA.*

D.M. Gavrila, "The Visual Analysis of Human Movement: A Survey", Computer Vision and Image Understanding, vol. 73, No. 1, Jan. 1999, pp. 82-98.

(Continued)

*Primary Examiner*—Brian P. Werner
*Assistant Examiner*—Jared W Radkiewicz
(74) *Attorney, Agent, or Firm*—William R. Conley

(57) ABSTRACT

A markerless method is described for tracking the motion of subjects in a three dimensional environment using a model based on linked kinematic chains. The invention is suitable for tracking robotic, animal or human subjects in real-time using a single computer with inexpensive video equipment, and does not require the use of markers or specialized clothing. A simple model of rigid linked segments is constructed of the subject and tracked using three dimensional volumetric data collected by a multiple camera video imaging system. A physics based method is then used to compute forces to align the model with subsequent volumetric data sets in real-time. The method is able to handle occlusion of segments and accommodates joint limits, velocity constraints, and collision constraints and provides for error recovery. The method further provides for elimination of singularities in Jacobian based calculations, which has been problematic in alternative methods.

2 Claims, 12 Drawing Sheets

OTHER PUBLICATIONS

Cai, Q. and J.K. Aggarwal, "Tracking Human Motion in Structured Environments Using a Distributed-Camera System", IEEE Transactions on Pattern Analysis and Machine Intelligence, vol. 2, No. 11, pp. 1241-1248.

Plankers, R. and P. Fua, "Tracking and Modeling People in Video Sequences", Computer Vision and Image Understanding vol. 81, No. 3, pp. 285-302.

Badler, N.I., K.H. Manoochehri, and G. Walters, 1987. Articulated Figure Positioning by Multiple Constraints. *IEEE Computer Graphics and Applications* 7:6, pp. 28-38.

Kakadiaris, I.A., D. Metaxas, and R. Bajcsy, Jun. 1994. Active Part-Decomposition, Shape and Motion Estimation of Articulated Objects: A Physics Based Approach. *Proceedings of the IEEE Conference on Computer Vision and Pattern Recognition*, Seattke, WA.

Metaxas, D. and D. Terzopoulos, 1993. Shape and Nonrigid Motion Estimation through Physics-Based Synthesis. *IEEE Transactions on Pattern Analysis and Machine Intelligence* 15:6, pp. 590-591.

Cheung, K.M., et al., Jun. 2000. A Real Time System for Robust 3d Voxel Reconstruction of Human Motions. *Proceedings of the IEEE Conference on Computer Vision and Pattern Recognition*, Hilton Head, SC.

Bottino, A. et. al., "A Silhouette Based Technique for the Reconstruction of Human Movement: A Multiview Approach", Jun. 1996, Proceedings of the IEEE Conference on Computer Vision and Pattern Recognition, San Francisco, CA.

Small, D.E. et. al, "Volumetric Video Motion Detection for Unobtrusive Human-Computer Interaction", Sandia Report, SAND2002-0801, Apr. 2002.

Bouguet, J.-Y., Jan. 4, 2004, "Camera Calibration Toolbox for Matlab" [online] [retrieved on Feb. 12, 2004] retrieved from the Internet: URL:http://www.vision.caltech.edu/bouguetj/calib_doc/.

McConville, J.T., et. al., "Anthropometric Relationships of Body and Body Segment Moments of Inertia", Report #AFAMRL-TR-80-119, Air Fore Aerospace Medical Research Laboratory, Ohio, Dec. 1980.

Luck, J.P., "Real-Time Markerless Human Motion Tracking Using Linked Kinematic Chains", Doctor of Philosophy Thesis, Department of Engineering Systems, Colorado School of Mines, 2003.

\* cited by examiner

REAL TIME MARKERLESS MOTION TRACKING USING LINKED KINEMATIC CHAINS

CROSS REFERENCE TO RELATED APPLICATIONS

This application claims the benefit of U.S. Provisional Application No. 60/452,773 filed on Mar. 7, 2003.

FEDERALLY SPONSORED RESEARCH

The Government has rights in this invention pursuant to Department of Energy Contract No. DE-AC04-94AL85000 with Sandia Corporation.

BACKGROUND OF THE INVENTION

The present invention relates to markerless methods for tracking the motion of a subject within a 3-dimensional (3D) space. The subject can be a human form or any form that can be modeled by a structure comprised of rigid linked segments, referred to in the art as linked kinematic chains. Linked kinematic chains are representations of non-deformable segments of the form being tracked. For example; a model of a human form could comprise rigid geometric segments, ellipsoids and cylinders, representing the head, torso, and limbs, mechanically interconnected by flexible joints that provide for rotation and angular positioning between the segments. Examples of subjects the method is applicable to tracking include but is not limited to humans, robots, laboratory animals, construction cranes and mechanical arms. The workspace within which the subject is moving, is divided into a plurality of smaller volume elements or voxels. The subject to be tracked is viewed by a system of multiple, video imaging cameras whose outputs are digitally acquired and processed on a personal computer. The method extracts silhouettes of the subject in each of the cameras views using background subtraction methods. A method is described for intersecting the multiple silhouettes to create a three dimensional volumetric data set, comprising a listing of the voxels within the workspace that are occupied by the subject. Volumetric data is collected in real time on a frame by frame basis. As the subjects motion is tracked from image frame to image frame, subsequent volumetric data indicates the new location of the subject as occupied voxels lying outside the previously computed location of the model. This new voxel data set is used to calculate virtual forces exerted on the model which act to align the model with the new voxel data set. This novel, physics-based tracking approach reduces the number of local minima that has hindered prior methods. The linked nature of the model additionally provides for tracking of partially occluded limbs. The model in the current method is dynamic and size parameters of the linked rigid segments are determined automatically by a growing process, during an initialization phase. A similar growing process is used to reacquire tracking if portions of the body are lost during tracking due to occlusion or noise. The dynamic model also incorporates velocity, joint angle, and self-collision limits. In an example embodiment, an imaging system with four cameras and a single PC operates the method in real-time at about 18 frames per second. The method describes a process for extracting volumetric data from a video imaging system, using the data to initiate dimension and initial positioning of a model template and an iterative process for aligning the model to subsequent data sets, acquired from each frame of the image, as the subject moves through a workspace. Three dimensional volumetric data is used to calculate forces acting on the model in three dimensions, which provides for a substantial improvement in tracking accuracy over prior methods performing force calculations in two dimensions, with or without multiple cameras.

In the following description of the invention, the method is applied to an embodiment for tracking human motion within a workspace. It will become obvious to one skilled in the art that the method is generally applicable to tracking the motion of any subject that can be modeled as rigid linked segments. Additional benefits to modeling the subject as a series of linked kinematic chains, as opposed to methods using a deformable model, will become apparent. An example of a method incorporating a deformable model can be found in U.S. Pat. No. 6,574,353 to Schoepflin et. al.

Video based 3D motion tracking is an active research topic. An overview of the field and this invention, including related references, is provided in J. P. Luck, "Real-Time Markerless Human Motion Tracking Using Linked Kinematics Chains", *Doctor of Philosophy Thesis, Department of Engineering Systems*, Colorado School of Mines, 2003, which is herein incorporated by reference in its entirety.

The need to improve man-machine interaction has made real-time markerless 3D motion tracking a highly valued goal. Current motion capture systems and methods require the subject to attach either magnetic or optical markers to their body and may even require cables extending from the markers to the system. Obviously a markerless method that does not require the user to wear specialized equipment would be more convenient, less constraining, more desirable, and in many cases necessary for the multitude of applications of such a process. These applications include:

Surveillance—In many surveillance situations such as access control, parking lot monitoring, ATM machine monitoring, or monitoring of publicly displayed valuables, it is helpful to not only know if humans are present but more importantly what they are doing.

Motion analysis—Motion analysis is extremely helpful in medical and biomechanical applications for the analysis of both injuries and the rehabilitation of injuries. Motion analysis has also become prevalent in sport applications. Analysis of swing can greatly improve a player's performance in golf, tennis, baseball, etc. A tracking system could also provide useful information in dance or ballet.

Virtual reality and video games—Tracking the human form is necessary to create interactive virtual environments. A tracking system could also be used for video games in which the user actually performs the motions of his or her screen character.

Teleconferencing—A virtual 3D teleconference could occur in real-time, because of the low bandwidth associated with transmitting joint angles.

Human robot interaction—Utilizing gesture control of systems, this type of tracking system would greatly enhance robot machine interaction. In industry typically safety constraints do not allow humans to enter spaces where large robots are performing tasks. However if the robot control system had knowledge of where the person was and what he or she was doing, the two could work together to perform tasks.

Advanced user interfaces—If a virtual interfaces are to be designed, the user must be tracked so that the system will know which virtual controls are being manipulated.

This vast array of applications presents many challenges to motion tracking. A system must be fast enough to collect data and track the subject in real-time. The system architecture must be relatively inexpensive and simple to be used for most applications—i.e. a system requiring expensive cameras and/or multiple computer architectures are of little use. The system must also be able to acquire the model on its own, and track unconstrained movement without the use of markers or specialized costumes.

Due to the growing number of applications for such a system, there has been a fair amount of interest in this field. For an excellent review of the state of the art of visually based motion tracking, see: D. M. Gavrila, "The Visual Analysis of Human Movement: A Survey", Computer Vision and Image Understanding, Vol. 73, No. 1, January 1999, pp. 82-98. Gavrila's review groups work within the art of video based motion tracking into four categories:

2D tracking approaches 3D tracking approaches using a single viewpoint 3D tracking approaches using multiple viewpoints 3D tracking approaches using 3D data.

Of course, some approaches may only slightly correspond to a particular category or may overlap two or more categories, but Gavrila provides a general framework for distinguishing the work and drawing comparisons between approaches.

2D Tracking Approaches The most simplistic process for acquiring the movement of a human in 2D is to assume that the movement can be accurately described with low-level 2D features, and hence there is no need for a model of the body. These techniques usually superimpose a grid over the region of interest, and extract low-level features for each region of the grid, such as normal flow, the number of foreground pixels, or an averaged edge vector. These techniques are adequate for many gesture interpretation tasks. However this type of approach is not accurate or robust enough for detailed tracking of a human model, mainly due to its inability to deal with occlusion.

More accuracy is achieved by using a simple body model. Many of these approaches use a simple model to identify the locations of segments in the image silhouette or outline. Some simply try to label segments using models based on: the order of segments, heuristics and learning of normal body outlines, generic postures of a human, a stick figure model of a human, or protrusions in a human outline. Others actually track segments in the silhouette using Kalman filtering, or simply track the contours of the human outline. While these approaches demonstrate the many ways a simplistic body model can be utilized in tracking, they only provide a coarse estimate of segment locations.

In order to gain further accuracy in 2D approaches, many researchers migrated to more descriptive models of the body. The motivation was that by expanding the model to include the size, shape, and connectivity of the subject, many ambiguities could be resolved. Techniques use a wide variety of data in their tracking and create a model to correspond to the data source. Silhouette based techniques incorporated the size, shape, and connectivity of segments to label their locations in the image, or tracked models consisting of either anti-parallel lines or "ribbons" (the 2D analog of a generalized cone). Optical flow based techniques align a 2D planar model to optical flow data. Another technique tracks a model consisting of blobs using motion and other low level features, such as color and shape. A degree of robustness is added by incorporating a more descriptive human model. However since the human is a three-dimensional object its shape changes depending upon its orientation to the camera; hence accurate 2D models are difficult to create. The problem is further complicated because segments move in and out of occlusion. One team attempted to mitigate this problem by switching between camera views, see: Cai, Q. and J. K. Aggarwal, "Tracking Human Motion in Structured Environments Using a Distributed-Camera System", IEEE Transactions on Pattern Analysis and Machine Intelligence, Vol. 2, No. 11, pp. 1241-1248. However, there are many poses in which relevant information cannot be found for all body segments from single view point. Another method using 2D data is described in U.S. Pat. No. 6,492,986 issued to Metaxas et. al. Again, the difficulties encountered in applying 2D data to a 3D model are inherent in this approach and it also describes a deformable model.

2D tracking has shown the ability to interact with computer systems as long as segments are in view of the camera. However in his review Gavrila concludes that 2D approaches are only effective for applications where precise pose recovery is not necessary, and most applications actually require the 3D pose of the subject. Consequently researchers have strived to extend tracking to 3D.

3D Tracking Approaches using a Single Viewpoint A large portion of the research in single viewpoint 3D tracking endeavors to simply extend the methods used for 2D analysis. Researchers again attempted to track features on the human to establish a 3D pose. However, joint locations show no characteristic intensity function; hence their locations are usually found indirectly by segmenting adjoining segments, which is extremely difficult and again complicated by occlusion. Accordingly many researchers extend 2D outline-based techniques to a 3D model. Researchers also attempted to employ optical flow to track the subject. Both approaches are usually performed by projecting the 3D model to the 2D image, and adjusting the model pose to fit the silhouette or optical flow data. However problems can occur when alignment forces are calculated in the 2D image and applied to a 3D model. 2D forces cannot account for changes in the model's appearance when it is twists about an axis that is not perpendicular to the image plane; hence the resulting model forces are often incorrect. Also optical flow can only be calculated within the image plane and alignment forces perpendicular to the image plane are very difficult to calculate from silhouette data; hence the process have problems estimating movement towards or away from the camera.

Researches also incorporated additional data sources to the above techniques to improve tracking results. Additional data sources include: locating the head and hands using skin color, using an occlusion map to indicate when a particular body segment is occluded, propagating constraints through the linked model, or using color and inverse kinematics to refine the hand position. Including additional data sources gains robustness because when one data source is insufficient to establish the pose the other can help.

Since all of these optimization schemes are susceptible to local minima, others have introduced the idea of multiple hypothesis tracking to find the correct solution. In this case, an optimization is run from more than one starting point using directions of high uncertainty in a Hessian matrix. While this addition greatly slows the process, it achieves some robustness to local minima, which is lacking in most approaches. The process works by restarting the optimization from several different poses and choosing the solution with the lowest error score. Because of the difficulty in finding reasonable starting poses and because the optimization must be rerun for each starting pose, the technique has not been made efficient enough to run in real-time.

Although these methods represent some improvement, such as applying forces to adjust a model, combining data sources, and incorporating multiple hypotheses, three major problems inhibit single viewpoint techniques. First, the problem of dealing with occlusion in a single viewpoint has not been robustly solved. For example if a person is turning around, these process will not be able to track any limbs behind the body. Although techniques that switch between cameras ease this problem, in many poses there is no single viewpoint from which one can accurately see all of the limbs. Secondly, 2D forces cannot account for changes in the model's appearance when it is twists about an axis that is not perpendicular to the image plane. Lastly, even when a single viewpoint method is able resolve the correct orientation of the articulated models, it still has difficulty establishing the actual 3D position. Many of these methods must know the actual size of the model to extrapolate the 3D position, or they estimate the 3D position from a pre-calibrated CAD model of the room, or they attempt to resolve the 3D position by tracking points over multiple frames. Hence, single viewpoint techniques are not robust enough to track unconstrained movements.

3D Tracking Approaches using 2D Data Obtained from Multiple Viewpoints To avoid occlusion and resolve the depth of the subject, many researchers have moved to systems that obtain 2D data from several disparate viewpoints so that multiple sides of a subject can be seen at the same time. These approaches either combine fitting performed in multiple 2D images to get 3D, or calculate forces/adjustments in 2D and apply them to a 3D model.

Many approaches again center on the silhouette or body outline, or extend optical flow based tracking to multiple viewpoints. As in single view approaches several methods that combine data sources to track blobs representing each segment have been developed. Lastly others have employed a multi-hypothesis approach, which again adds robustness but is not able to operate in real-time. All of these techniques represent improvements; however problems often occur when transforming from the 2D image to the 3D world.

First, when fitting is performed in each 2D image and combined to get 3D, any error in the 2D fitting will propagate into the 3D result. Hence these approaches are subject to the same faults as their 2D counterparts. For instance if limbs are partially occluded in a viewpoint, the process may still attempt to fit the limb and do so incorrectly. When the results are combined from each 2D view these erroneous measurements will propagate into the 3D result. To avoid this problem the process would have to decide when an accurate fit cannot be obtained in a viewpoint, which is an extremely difficult problem. Then the process would have to rely on the measurements in the other viewpoints to obtain the 3D result, which may not be sufficient to resolve all ambiguities. Hence the approach must either attempt to estimate a 2D pose from incomplete information in a particular viewpoint, or ignore any information in that viewpoint and attempt to resolve ambiguities from fewer viewpoints.

Secondly, the inclusion of multiple viewpoints does not remove the problems seen in single viewpoint techniques of applying forces calculated in 2D to a 3D model. 2D forces or adjustments cannot account for changes in the model's appearance when it is twists about an axis that is not perpendicular to the image plane; hence the resulting model forces are often incorrect.

Lastly, combining information from multiple viewpoints is not a straightforward problem. Combining 2D poses to obtain a 3D pose is complicated because small changes in one viewpoint could account for a large change in others. Therefore how does one find the best 3D pose from multiple 2D estimates when they do not align perfectly, which will be the norm for real world data. Similarly when combining tracking information (adjustments or forces) from multiple 2D viewpoints, one must decide how to combine conflicting information from separate viewpoints.

3D Tracking Approaches using 3D Data Due to the problems of performing 3D fitting from 2D images, transforming 2D information to the 3D world, and of combining conflicting information from multiple viewpoints, it is preferred to work directly with 3D data. Several research teams use 3D data taken with a range finder or from stereo cameras. In particular one method of combining stereo points with silhouette data yields extremely accurate results, see: Plankers, R. and P. Fua, "Tracking and Modeling People in Video Sequences", Computer Vision and Image Understanding Vol. 81, No. 3, pp. 285-302. This method fits a model made up of "metaballs", which change shape to account for movement of the muscles. The technique cannot operate in real-time and requires user to help extract the silhouette, but again shows robustness through combining multiple data sources. However information from more than one viewpoint must be incorporated to overcome occlusion.

Others have employed constraint fusion to 3D data, see: "Badler, N. I., et. al, "Articulated Figure Positioning by Multiple Constraints", IEEE computer Graphics and Applications, Vol. 7, No. 6, pp. 28-38. The tracking process rely on feature detectors, which are unreliable and again can require combining conflicting information from multiple feature trackers. However the methods do demonstrate the value of including constraints in the tracking process.

In other methods, 3D points exert pulls on deformable models that are connected through linking constraints, see Kakadiaris, I. A. et. al., "Active Part-Decomposition, Shape and Motion Estimation of Articulated Objects: A Physics Based Approach", Proceedings of the IEEE Conference on Computer Vision and Pattern Recognition, June 1994, Seattle, Wash., and Metaxas, D. et. al., "Shape and Nonrigid Motion Estimation Through Physics-Based Synthesis", IEEE Transactions on Pattern Analysis and Machine Intelligence", Vol. 15, No. 6, pp. 590-591. These pulls adjust both the model shape and orientation through a Kalman filter framework, which incorporates the Jacobian matrix. Since the pulls are calculated in 3D, the problems of transforming a 2D force to a 3D model are avoided. The concept of using the data to pull the model into alignment is good if data is taken fast enough so that the change between data sets is small. The methods also demonstrate how the Jacobian matrix can be used to simplify torque calculations on a linked model. However several limitations of the methods must be overcome to obtain robust real-time tracking. First, using the Jacobian with a linked model usually implies singularities, which must be removed (see below). Second, data acquisition must also occur in real-time if tracking is to occur in real-time. Third, allowing the model to change shape with each data set can cause errors. If the model is allowed to conform to each data set, where for example, data along a limb becomes sparse for several frames, the model will become erroneous and can affect tracking in subsequent frames. The limb model will shrink and become erroneously small. When data along the limb returns (perhaps only a few frames later) the new points may project onto the body instead of the shrunken limb model and cause further errors.

Approaches by others have used shape-from-silhouette sensors to acquire 3D volume data, see Cheung, K. M., et. al., "A Real Time System for Robust 3D Voxel Reconstruction of Human Motions", Proceedings of the IEEE Conference on Computer Vision and Pattern Recognition, June 2000, Hilton Head, S C and, Bottino, A. et. al., "A Silhouette Based Technique for the Reconstruction of Human Movement: A Multiview Approach", June 1996, Proceedings of the IEEE Conference on Computer Vision and Pattern Recognition, San Francisco, Calif. The volumetric 3D data is acquired by intersecting silhouettes from multiple viewpoints. Although the reported tracking is poor with their methods, the work demonstrates that shape-from-silhouette data acquisition and tracking can both occur in real-time. Bottino's process is not able to run in real-time but provides useable results using synthetic data.

Limitations of Previous Work:

Need for 3D Data Utilization Techniques that do not use 3D data for tracking have inherent problems. Approaches using 2D data cannot overcome occlusion, have problems transforming 2D forces to a 3D model, and have difficulty establishing the actual 3D position or distance from the camera. Multiple viewpoint 2D techniques have problems performing 3D fitting in 2D, transforming 2D information to the 3D world, and of combining information from multiple viewpoints. Hence methods using 3D data are needed for development of a tracking system that can meet the requirements of all of the previously listed applications. However, several limitations of the reviewed 3D data approaches must be solved. The system must acquire data from several viewpoints, and do so in real-time without requiring markers or specialized clothing. Singularities must be removed if the Jacobian is utilized to relate changes in the data to changes in the model. Lastly, the model should not be allowed to change shape with each data set, but still must be robust enough to deal with varying data.

The model acquisition issue: Much of the previous work assumes that the 3D model is fully specified a priori and only addresses the pose recovery problem. In practice, the 3D model is parameterized by various shape parameters that need to be estimated from the images. Some work has dealt with the issue by decoupling the model acquisition and pose recovery, i.e. by requiring a separate initialization stage where either known poses or known movements simplify the acquisition of the shape parameters. Although some work represents a step forward on this matter, no method has been provided that can recover both shape and pose parameters from uncontrolled movement, e.g. the case of a person walking into a room and moving freely around.

The occlusion issue: Most methods cannot handle significant (self occlusion and do not provide criteria to stop and restart tracking of segments. There is no concept of pose ambiguity either.

The modeling issue: Human models for vision systems have been adequately parameterized with respect to shape and articulation, but few have incorporated constraints such as joint angle limits and collision constraints, and even less have considered dynamical properties such as balance. In contrast to graphics applications, they have made little or no use of color and texture cues to capture appearance. Lacking entirely is the ability to deal with loose-fitting clothes. Finally, there is also a need to model the objects the humans interact with.

The real-time issue: A system and method must perform data acquisition and tracking in real-time without requiring markers or specialized clothing to be useful for most applications. All of the applications listed above, outside of motion analysis require real-time analysis to be useful.

Expense and simplicity issue: Methods must be capable of operation on systems that are inexpensive and should not require large amounts of hardware to be set up and connected.

The calibration issue: The data acquisition process must be relatively simple and fast to calibrate. Methods must be provided that allow for system to be calibrated by someone who is uneducated in camera calibration techniques before they can be used outside of research. Calibration also needs to be relatively fast so that systems can be moved or changed without incurring large delays due to recalibration.

Each of the above references describes a method having unique capabilities, but no reference on it's own satisfies all of the required characteristics. There remains a need in the art for a more advanced and efficient method of motion tracking. It is therefore an object of this invention to provide a real time markerless motion tracking method utilizing linked Kinematic chains to fulfill this need.

BRIEF SUMMARY OF THE INVENTION

In an embodiment of the invention, a model template of a human form to be tracked in a 3D workspace is constructed of rigid geometric primitives, kinematic chains, connected via flexible joints. In this example embodiment, a new method utilizing four video cameras acquires 3D shape from silhouette data in real time of the form being tracked, see Small, D., et. al. "Volumetric Video Motion Detection for Unobtrusive Human-Computer Interaction", Sandia Report 2002-0801, April 2002, herein incorporated by reference in it's entirety. Volumetric data is used to initialize the model with correct segment sizing, location in the workspace and relative location of each model segment with respect to the other model segments. Once the model is initialized, volumetric data collected on a frame by frame basis is used to track the from through the workspace and update the model's positional information.

The data acquisition method as describe by Small et. al. utilizes a Real-Time-Shape-from-Silhouette Sensor, or $RTS^3$. In this method, the 3D workspace is divided into virtual cubes called "voxels". $RTS^3$ provides data in the manner of which voxels within the virtual workspace are occupied by the form being tracked, allowing a volumetric image of the visual hull of the form moving in the workspace to be created. The method provides for computing the size and location of the geometric primitives of the model by fitting the model to the volumetric voxel data. This data is provided at a rate equivalent to the framing rate of the imaging system being used. As the object being tracked moves between frames, the $RTS^3$ returns a data set of voxels shifted from the previous position of the computed model. If the form has moved, the new set of voxels lie outside the previous frames volumetric image of the form. The distance the later set of voxels are displaced from the previous frames model are used to calculate forces acting on the model, that act to pull the model into alignment with the new data set. The method includes joint limit, velocity, and collision constraints in the alignment of the model. These constraints are incorporated in a new post-processing scheme, which does not slow the process, and the method is used in real time.

An object of this invention is to provide a motion tracking method, which runs in real-time without the need for multiple computers, uses inexpensive video cameras and framegrabber cards to connect cameras to the computer, and does not require the use of markers or specialized clothing. In doing so the method is plausible for use in a multitude of applications. The method is based upon shape-from-silhouette data acquisition that is capable of acquiring 3D "voxel" data in real-time. This data is used to align a model with the actual pose of the subject. An alignment method utilizes a physical model, whereby the data pulls the model into alignment using a Jacobian based process.

Another object of this invention is to provide a method using volumetric 3D data for tracking purposes. The data is not actual range data due to sensor related drawbacks: high cost, low resolution, limited measuring range, safety concerns, and insufficient data acquisition speed. Instead 3D data is obtained through a triangulation based technique, which employs multiple (four in an example embodiment) cameras looking from different angles into the workspace to create a "visual hull" of any object within the workspace. Accordingly the problems of extrapolating a 3D pose from 2D information are avoided.

Another object of the invention is to provide for initialization of a model template without the need for a priori knowledge. To remove the limitation of having to define the model a priori, the approach provides two new methods for model initialization. The first requires the user to stand in an initialization pose from which it accurately measures the model parameters. The second method is able to autonomously estimate model parameters using anthropometric relationships between body segment sizes and the height and relative size of the user (automatically estimated when he or she enters the workspace). Alternatively the model parameters can be measured by hand and read in during initialization.

Another object of this invention is to provide a method to remove singularities in Jacobian based calculations of forces acting on a model.

It is another object of this invention to augment the Jacobian by including inertia equations to calculate accelerations on each joint due to the torques. This addition to Jacobian based tracking incorporates the size and shape of the model in the alignment process, instead of basing the adjustment purely on the pulls from the data.

Another object of this invention is to provide a novel iterative optimization scheme to pull the model from alignment with the previous data set into alignment with the current data set. The process is efficient enough to operate in real-time, which means the adjustment between data sets should be very small, thereby allowing this method to work reliably.

It is another object of this invention to provide joint limit, velocity, and collision constraints in the alignment of the model. The constraints are incorporated in an innovative post-processing scheme, which does not noticeably slow the process or affect the normal operation of the optimization. The tracking process is robust enough to deal with loose fitting clothes.

Another object of this invention is to provide a method for overcoming occlusion of a moving subjects limbs, by creating volumetric data using many camera views. Accordingly segments occluded in one or more camera view will not be occluded in all views. In addition the tracking technique is robust enough to deal with missing or erroneous data. Another object of the invention is to provide a technique to sense if tracking has failed, find a new estimation of the pose, and restart tracking.

To achieve the foregoing and other objects, and in accordance with the purpose of the present invention, as embodied and broadly described herein, the present invention comprises a method for combining data extracted from two dimensional images to obtain three dimensional, volumetric data, wherein the three dimensional data is used to calculate forces in three dimensions acting to pull a model into alignment with the volumetric data.

These and other objects of the present invention will become more fully apparent with reference to the following description and drawings, which relate to embodiments of the invention.

DETAILED DESCRIPTION OF THE INVENTION

Figure 1:
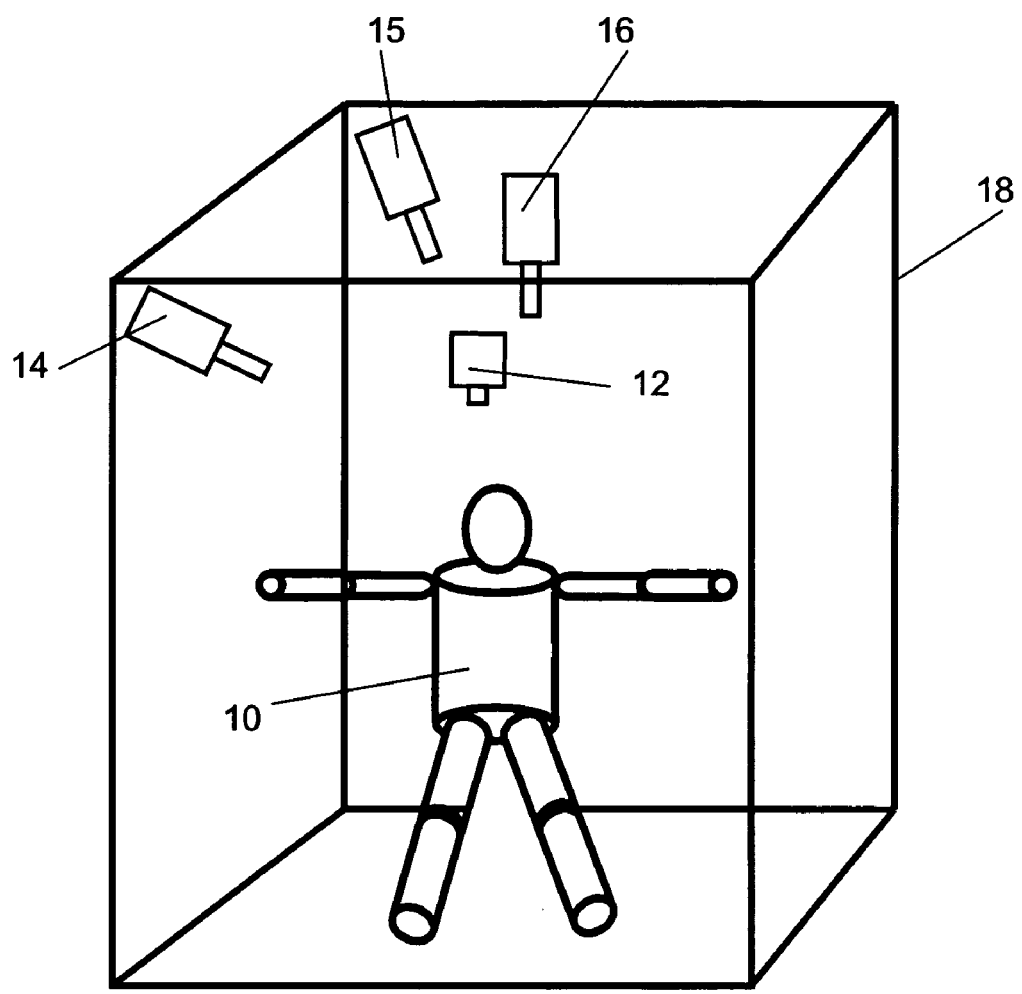
FIG. 1 Positioning of cameras within a workspace to track a subject

Video Imaging System: A video imaging system comprises a multiple of video cameras, frame grabber or data acquisition cards providing means for digitally capturing the camera images and a computer or similar means for digitally processing the images. As illustrated in FIG. 1, in an embodiment of the invention the method was applied to tracking a subject (10) within a thee dimensional workspace (18) using a video imaging system having a video camera (12) in the front of the workspace, two video cameras (14 and 15) located in corners of the workspace, and one video camera (16) located in the ceiling of workspace (16). In this embodiment of the method, color video cameras were used but monochrome cameras could be used as well, with some sacrifice in performance as will become apparent below. The video cameras in combination with four PCI-bus frame grabber cards (not shown) and a personal computer (not shown) comprise a video imaging system, commonly referred to as a Real-Time-Shape-from Silhouette Sensor. The video imaging system used in the example embodiment is described in the reference; Small, D., et. al., "Volumetric Video Motion Detection for Unobtrusive Human-Computer Interaction", Sandia Report #SAND2002-0801, April 2002 incorporated by reference herein in it's entirety. It will become obvious to one skilled in the art that any video imaging system, or data acquisition system that provides volumetric data, could employ the tracking method of the present invention as well. As described by Small et. al., volumetric data, is collected by the Real-Time Shape-from-Silhouette Sensor, or $RTS^3$. This sensor uses a combination of industry standard components including a high-end PC, four-color video cameras, and four PCI-bus frame grabber cards. Windows NT was used to allow different video cameras or frame grabber cards to be used (the system also runs on Windows 2000, or other operating systems). The $RTS^3$ in the present example uses a Dell Dimension single processor 2.2 GHZ machine with 512 Meg of RAM, four Javelin Pro CCTV Cameras, and four Imagenation PXC200 color frame grabber cards. However using different cameras or frame grabber cards would not affect the process, and using a slower computer will only slow the data acquisition rate. Using this hardware, the system creates a time-varying volumetric image of the visual hull of any object moving in the space observed by all four cameras. Locating the cameras (12), (14), (15) and (16) high within the workspace (18) as shown in FIG. 1 provides for imaging as much of the workspace volume as practical. The location and positioning of the cameras is not critical to the method. As will become obvious in the following description, any number of cameras, greater than one, could utilize the methods as described herein.

Figure 2:
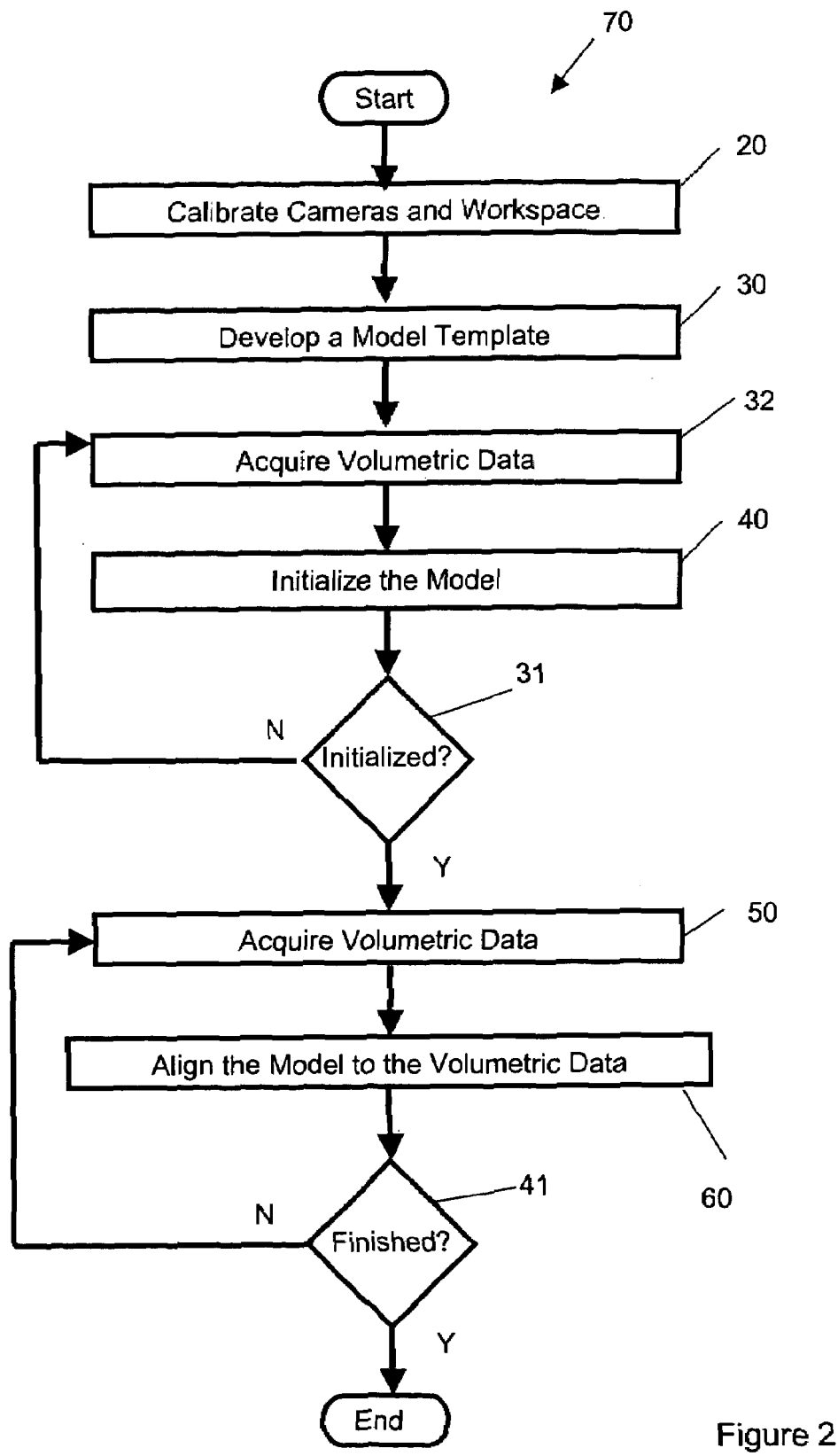
FIG. 2 Block Diagram Of the Markerless Motion Tracking Method

FIG. 2 is a block diagram of an embodiment of the real time markerless motion tracking method using linked kinematic chains (70), comprising the steps of; calibrating cameras and workspace (20), developing a model template (30), acquiring volumetric data (32), initializing the model (40), acquiring volumetric data (50) and aligning the model to the volumetric data (60). In the method, volumetric data (32) is acquired from the first frame or first few frames of viewing the subject in a workspace and is used to initialize a model of the subject. After the model is initialized, volumetric data is collected from subsequent frames (50) and is used in aligning the model within the workspace. The process of acquiring volumetric data is the same in both steps.

Calibration of cameras and workspace: In FIG. 2, step (20) involves determining the intrinsic and extrinsic parameters of each camera comprising the video imaging system, partitioning the workspace volume into small volume elements, voxels, mapping the voxels to each pixel subtended in each of the cameras, and acquiring an averaged background or reference image of the workspace for each camera. The $RTS^3$ system requires an accurate calibration of each camera's intrinsic and extrinsic parameters in order to generate 3D data. The intrinsic parameters include the x and y focal lengths, the location of the center pixel, the 1st and 2nd coefficients of radial distortion, and the 1st and 2nd coefficients of tangential distortion. The extrinsic parameters are simply the transformation from the camera coordinate system to a world coordinate system, the world coordinate system being the coordinate system of the workspace. The calibration step (20) uses methods developed in the camera calibration toolbox for Matlab®. The C implementation of the toolbox, well known in the art, is publicly available in the Open Source Computer Vision Library, see Bouguet, J.-Y., Jan. 4, 2004, "Camera Calibration Toolbox for Matlab®" [online] [retrieved on Feb. 12, 2004] retrieved from the Internet: <URL:http://www.vision.caltech.edu/bouguetj/calib_doc/>. The method provided by Bouguet is used to estimate the intrinsic matrix, the tangential distortion, and radial distortion parameters using a series of snapshots of a checkerboard pattern. The checkerboard represents a three dimensional rigid body that lies on a plane. Several images are recorded with the checkerboard at different rotation and tilt angles between the image and target planes, and the interior corners of the checkerboard are located to sub pixel accuracy. The intrinsic parameters are computed using an iterative non-linear least squares method, which successively estimates the intrinsic matrix and the relative position and orientation of the checkerboards with respect to the camera.

Once the intrinsic parameters have been determined, a similar process is used to solve for the extrinsic parameters, that is the location of the cameras in the coordinate system of the workspace. The extrinsic parameters for each camera are solved for by observing a common set of planar targets of know location, and correlating each 2D point in each cameras image of the target, with the targets known 3D world coordinate. In the present embodiment of the invention, small 2 inch×2 inch checkerboards were attached to regularly spaced linoleum, which is rolled out on the floor of the workspace.

Each camera's extrinsic parameters are estimated by observing the same planar points; hence all cameras are calibrated with respect to the same world coordinate system. In this process the user selects specific planar target points on a ground plane and associates them with 3D points stored in a text file. Once all targets are selected the extrinsic parameters for each of the cameras is calculated.

Once the intrinsic and extrinsic parameters of each camera have been determined, the next step is to calibrate the workspace volume observed by all the cameras. The workspace volume is partitioned into small cubes or voxels. A look-up table is created relating each voxel to a position in each cameras image. In brief, each voxel centroid position is back-projected into each of the camera images using the extrinsic and intrinsic calibration for that camera. The process to create the individual look-up tables takes an (x, y, z) triplet and a camera's parameters, and returns the pixel, (u, v), that the centroid of the voxel maps to. In this manner, each pixel in each cameras image plane is mapped to a voxel within the workspace.

After the cameras and workspace volume have been calibrated, a background image of the workspace is obtained for each camera. Several images of the workspace are obtained for each camera and are averaged to produce a reference or background image of the workspace for each camera. Color images are taken so that for each pixel in each averaged image, the hue of the background as well as the average intensity are known.

Acquiring Volumetric Data: After calibration of the cameras and workspace, volumetric data acquisition can proceed. Volumetric data comprises information in three dimensions that describes the space a subject is occupying. Acquiring volumetric data is a process undertaken for each frame of the video of the subject within the workspace. An initial volumetric data set (32) is acquired from the first video frame or can as well comprise data from a multiple of initial frames and is used to initialize (dimension and position) a model of the subject within the workspace, FIG. 2, step (40). Subsequent data sets are obtained from image frames of the subject after the initialization process is completed, and are employed in tracking the subject which comprises the steps (50) and (60). Volumetric data provides a listing of which voxels within the workspace are either occupied by the subject, or empty.

Acquiring volumetric data comprises;
    extracting silhouettes from the four images from each of the four cameras, using an adaptive background subtraction and thresholding process. This process indicates which pixels have statistically changed from the background image for that camera, to create a silhouette of the subject in each of the cameras and,
    intersecting the silhouettes to obtain an approximation of the volume the subject is occupying. This provides a listing of which voxels within the workspace are occupied by the subject.

To make the system run in real-time a digital approximation of the volume is used. The workspace is filled with virtual cubes, voxels, which represent the volume. Voxels can be either occupied, by the subject, or empty. To decide whether a voxel is occupied or not, look-up tables are created that relate every voxel to a pixel in each of the cameras. Then, by traversing the voxels and examining the appropriate image-pixels, one can tell which voxels are occupied. Occupied voxels will have the appropriate pixel in each of the cameras labeled as part of the silhouette. The result is a very fast, low-latency system that is appropriate for tracking work.

Silhouettes are extracted using an adaptive background subtraction technique. The basic idea of background subtraction is to compare current images taken from a stationary camera to an original background image. Any pixels that differ from the background are labeled as part of the silhouette. To alleviate the affects of camera noise, pixels are compared to the mean and standard deviation of the pixel values from many background images.

The process includes color for extra discrimination power and incorporates a hue angle check to avoid shadows. The key assumption used for eliminating shadows through hue differencing is that an area where a shadow is cast may show a change in intensity but will only show a small change in hue. Accordingly any pixel in doubt, with an intensity change greater than a lower intensity threshold, $I_{lower}$, and a high upper intensity threshold, $I_{upper}$, must have a large change in hue, greater than $\Delta H_{thresh}$, to be considered part of the silhouette.

Upper and lower intensity bounds are used to quickly distinguish obvious background and silhouette pixels, and to aid in discrimination the $RTS^3$ process analyses all three-color bands separately. Hue differencing is then incorporated to avoid shadows. Any remaining pixels are compared to the standard deviation of each color band of each pixel for final characterization. Afterwards small holes are filled using a contouring process that decomposes a binary image into a two level hierarchy of contours: exterior contours and their interior holes. Interior contours are filled to remove holes, and small exterior contours are removed from the silhouette, which removes speckled data points.

When silhouettes from several different viewpoints are intersected the result is a 3D visual hull of the object. For this method to perform data acquisition, tracking, and provide visual feedback all in real-time on a single computer, the process has to be extremely efficient. To achieve this a digital approximation of the visual hull in the form of voxels (small virtual cubes) is used. Voxels fill the workspace and are associated with a binary value that indicates whether the voxel is occupied or empty. An occupied voxel means the voxel is contained within an object, within the workspace. The dimensions of the voxels regulate the accuracy of this approximation.

To further speed data acquisition the $RTS^3$ system creates look-up tables that relate each voxel to a pixel in each of the cameras. Therefore all that needs to be done to intersect the silhouettes is to traverse through the voxels and inspect the appropriate pixels in each camera. If the corresponding pixel in each of the cameras is part of the silhouette, the voxel is part of the visual hull and is considered occupied.

Figure 3:
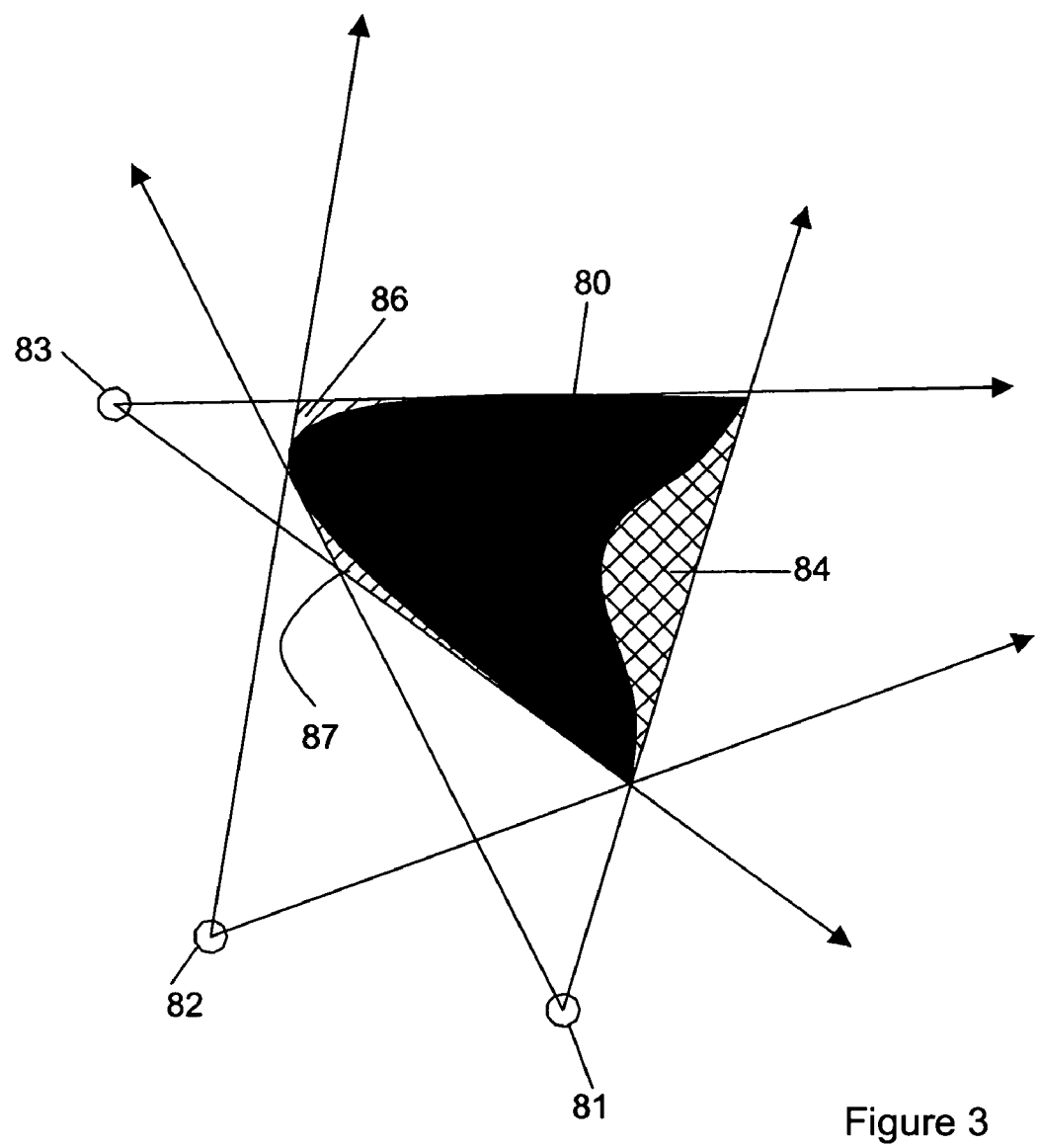
FIG. 3 Multiple Camera Shape From Silhouette

The method is able to produce 3D data quickly enough for real-time implementation, however the method produces a visual hull, which is not an exact representation of the volume occupied by a subject FIG. 3. As the cameras (81-83) view an object (80) from outside of the object, there is no placement of these three cameras that will discern concavities (84). Additionally tailing points (86) and (87), which are not in view of any of the cameras, will be included in the visual hull. The more cameras that are employed, the more accurate the volumetric data will be in representing the actual subject. In the example embodiment, four cameras were used but it is anticipated that any number of cameras greater than one could be used.

Figure 4:
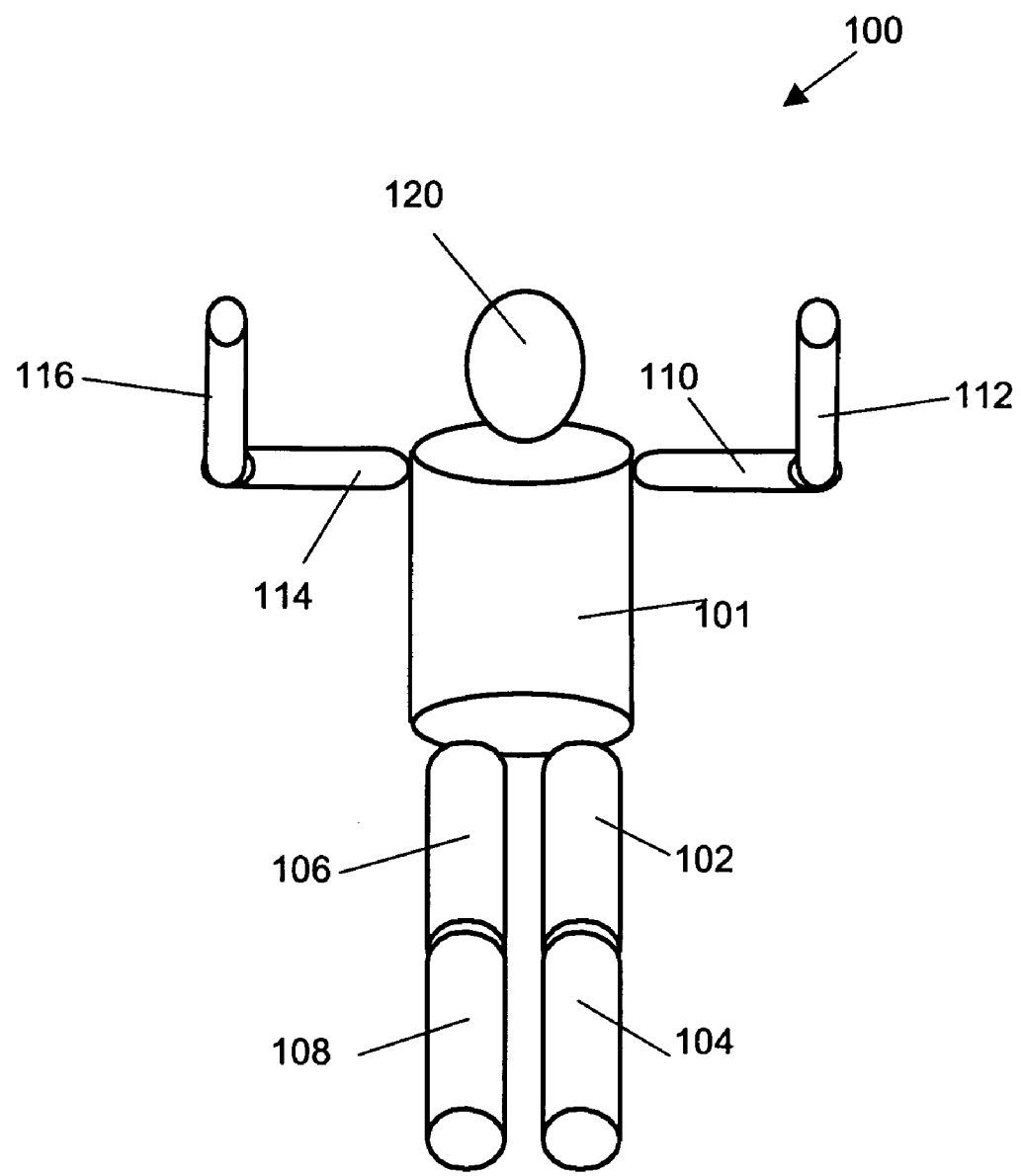
FIG. 4 A Model Template for a Human Form

Developing a model template: Developing a model template, FIG. 2 step (20) establishes the set of linked geometric shapes commonly referred to as linked kinematic chains, that are used to represent a subjects form. The model template tells the method what shapes to apply the volumetric data to. A model template contains no dimensional or positional information. Once a model template is fitted to volumetric data as during the initialization step (40) a model is said to have been constructed. FIG. 4 illustrates a model template (100) appropriate for an embodiment where a human form is to be tracked. It should be understood that any model template comprising rigid segments linked by flexible joints could be used by the method and is selected as appropriate for the subject being tracked, whether the subject be a robot, laboratory animal, construction crane, mechanical arm, etc. In the present embodiment for tracking a human form, a cylindrical ellipse, is used to represent the torso (101) (an ellipse when viewed from above and a cylinder when viewed from the side), cylinders are used to model each of the limb segments (102-116), and an ellipsoid represents the head (120). The model contains four rotational degrees of freedom (DOF) in each limb (102-116), three rotational DOF for the head (120) and six DOF, comprising 3 translations and 3 rotations, in the torso (101). Once the template has been initialized, the model as comprised of rigid segments, do not change shape or size during tracking, only translation within the workspace and rotation of the segments about the joints.

Figure 5:
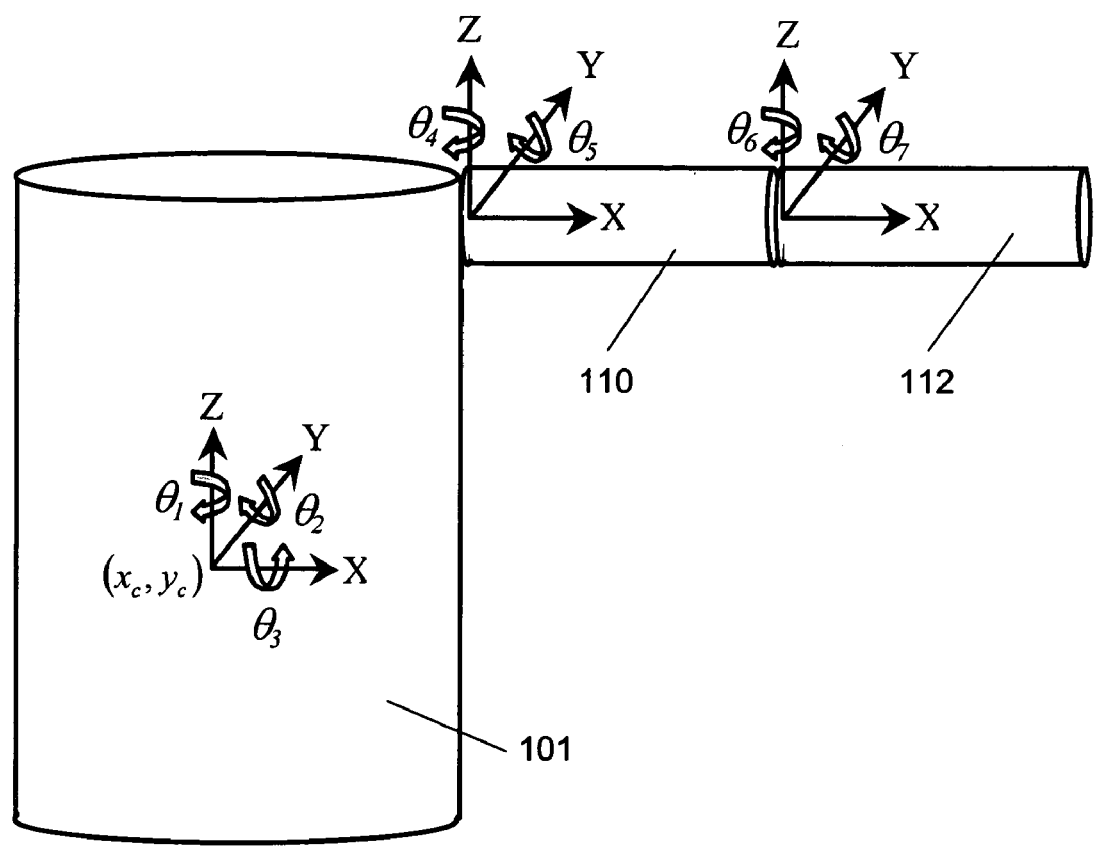
FIG. 5 Model Coordinate Systems and Rotation Angles

The limbs FIG. 4 (102-116) in the example embodiment are modeled in a novel manner. Instead of using a configuration with three rotations at the shoulder or hip and one rotation at the elbow or knee (three by one) as in an actual human, the model configuration employs two rotations at each joint (two by two) as shown in FIG. 5. The benefits to this approach will become clear below. The two configurations have identical articulation spaces, and because cylinders are used to model the limbs, the shapes of the segments are identical in all poses. Rotations about joints are modeled by an accumulation of Euler angles whereby successive rotations occur about the current axis position as defined by all preceding angles. In the model, the rotations move out from the torso to the shoulder/hip and lastly to the elbow/knee. FIG. 5 shows how the rotations proceed for the upper body segments of the model. Rotations of the Torso (101) are Z-Y-X Euler angles ($\theta_1$, $\theta_2$, $\theta_3$) and upper limb (110) rotations are Z-Y Euler angles ($\theta_4$, $\theta_5$) lower limb (112) rotations are Z-Y Euler angles ($\theta_6$, $\theta_7$). The zero position for the torso (101) has the torso aligned with the world coordinates ($X_c$, $Y_c$). The zero position for a limb (leg or arm) has the limb extended out along the x axis of the torso.

Initializing the Model: Volumetric data from the initial frame or frames of the imaging system is used to initialize, determine the dimensions and initial position of, the model template. Two methods have been developed for initializing the model, FIG. 2 step (40):

The first technique, initializing the model from pose, requires the subject to perform an initialization pose upon entering the workspace. The pose as shown in FIG. 1, is a stance in which body segments are in clear view (standing erect and facing an approximate direction with arms extended to the sides and legs separated from one another), so that the parameters of each body segment can be measured.

The second technique, autonomous model initialization, uses anthropometric relationships and assumes the subject is standing erect and facing towards the middle of the workspace when the subject enters the workspace.

When a sufficient number of voxels has been acquired during the volumetric data acquisition process, the routine will try and initialize the model. In the example embodiment of tracking a human form, the method begins by segmenting out the torso, FIG. 4, (101). The routine used assumes the (x, y) center of the torso, ($x_c$, $y_c$), is at the median of all of the voxels, which should be true if the user is standing in the initialization pose. The routine then slowly increases the radius of an infinite cylinder centered at ($x_c$, $y_c$) until the number of voxels added to the cylinder drops off significantly, which should happen once the radius is increases beyond the shoulders. Once this occurs an ellipsoid is fit to all the voxels within the cylinder and between the shoulder bridge and the crotch of the subject. The shoulder bridge is at the highest point, max(z), near the radius of the torso: $\sqrt{(x-x_c)^2+(y-y_c)^2} \approx r_b$. The crotch is at the lowest point, min(z), directly below the center of the torso: $\sqrt{(x-x_c)^2+(y-y_c)^2} \approx 0$. The ellipsoid is computed by performing an eigenvalue decomposition of the moment matrix M. The eigenvectors correspond to the directions of the principal axes of the ellipsoid, and the eigenvalues correspond to the dimensions of the ellipsoid along each axis.

$$M = 4 \begin{bmatrix} M_{xx} & M_{xy} & M_{xz} \\ M_{yx} & M_{yy} & M_{yz} \\ M_{zx} & M_{zy} & M_{zz} \end{bmatrix} \text{ where, } M_{ab} = \frac{1}{n}\sum_{i=1,n} a_i b_i.$$

The ellipsoid is used to determine the thickness and width (x, y) of a cylindrical ellipse used to model the torso (101), while its height is taken as the distance from the shoulder bridge to a point the radius of the leg above the crotch. Lastly the directions of the principal axes are used to determine the three rotations of the torso.

Growing Process: Remaining voxels are used to estimate the dimensions of the head (120) and limbs (110-116). Since it is known that the limbs are extended away from the body a growing process can be started from their respective joint centers on the torso (shoulders and hips). The growing process, iteratively expands to include any voxel that is outside of the torso, on the correct side of the body, and neighbors any voxel that is already included in the limb voxels. An ellipsoid is fit to this data to estimate the radius of the limb, and the limb length is set to the distance between the torso and the voxel (found in the growing process) furthest from the torso. Joint angles at the shoulders and hips are determined from the vector extending from the joint center to this voxel, and joint angles at the elbows and knees are initialized to zero (fully extended).

Lastly the head (120) parameters are estimated. This is done by fitting an ellipsoid to all voxels above the shoulder bridge and between the two shoulders. Since the head is modeled as an ellipsoid the fit yields all head parameters: thickness, width, height, and orientation: roll, pitch, and yaw.

To insure that subject is standing in the initialization pose several checks are made as each segment is estimated. The torso (101) is checked to see if it is of reasonable size, if the user is completely inside of the workspace, and if the user is facing the correct direction. Each limb (110-116) is checked to see if it is of reasonable width and thickness and if it is within a certain joint limit range (i.e. it is in the proper pose). Lastly the head is checked to see if it is of reasonable size. If any of these checks fail the process waits for the next set of data, next frame, and repeats the initialization phase.

Autonomous Model Initialization: An initialization scheme, which does not require the user to stand in an initialization pose, was also developed for use in applications where an initialization pose is unfeasible. The routine bases model parameters off of anthropometric relationship data, relative to the height and general size of the subject see McConville, J. T., et. al., "Anthropometric Relationships of Body and Body Segments Moments of Inertia", Report #AFAMRL-TR-80-119, Air Force Aerospace Medical Research Laboratory, Ohio, December 1980. With this routine only a few assumptions must be made about the pose of the user to initialize. The user must be standing erect and not have his or her arms extended above the head so that the height of the subject can be assessed. Also the subject must enter the workspace facing forward or the system will initialize with the model facing 180 degrees from the proper alignment.

Again, when a sufficient number of voxels has been acquired during the volumetric data acquisition process, the routine attempts to initialize the model. First the routine must assess the height of the subject. To do this the routine assumes the subject is standing straight up when entering the workspace and therefore the highest voxel associated with the subject is taken to be the height of the person. Next an ellipsoid is fit to the data so that the thickness (front to back) and width (shoulder to shoulder) of the subject can be determined. From these three measurements the dimensions of the entire body are estimated using anthropometric relationship data, shown in Table 1. The subject must be standing straight up and not have his or her arms extended above their head or the estimated height and hence all subsequent estimates will be erroneous.

TABLE 1

Listing of autonomous initialization parameters.

| Segment | Height | Width | Thickness | Orientation | Center |
|---|---|---|---|---|---|
| Torso | SubjectHeight − Head Height) | Ellipsoid Fit (shoulder to shoulder) | Ellipsoid Fit (chest to back) | Ellipsoid Fit | xy = Median z = SubjectHeight/2 + TorsoHeight/2 |
| Head | SubjectHeight/10 | TorsoWidth/2 | TorsoWidth/2 | Assume looking straight forward | Assume straight above torso |

| | Length | Radius | Joint Position | | |
|---|---|---|---|---|---|
| Upper Arm | (SubjectHeight − TorsoWidth)*.225 | Upper leg radius/2 | (torso coordinates) x = +/− TorsoWidth/2 y = 0 z = TorsoHeight − UpperArmRadius | Growing Process | |
| Lower Arm | (SubjectHeight − TorsoWidth)*.275 | Lower leg radius/2 | End of upper arm | Growing Process | |
| Upper Leg | (SubjectHeight)/4 | TorsoWidth/6 | (torso coordinates) x = +/− TorsoWidth/4 y = 0 z = −TorsoHeight | Growing Process | |
| Lower Leg | (SubjectHeight)/4 | Torso Width/8 | End of lower arm | Growing Process | |

The pose of the subject is determined in much the same manner as the "initialization from pose" routine. The routine estimates the orientation of the torso by again fitting an ellipse to the torso and attempts to find the limbs using the growing process described above. However since an initialization pose is not required, a check must be made to determine if either arm is lying alongside the torso. If the arms are lying alongside the torso, the estimate for torso width will be too large and the routine may not be able to discern the orientation of the arms. Accordingly when the growing process attempts to find the arms, if either arm is found alongside the torso or is not found (which normally occurs if an arms is lying alongside the torso), the torso straight down alongside the torso, and is considered to be lost. Tracking begins but a recovery process continues to search each new data set until the arm is located.

As in the "initialization from pose" routine, checks are made to insure the initialization measurements are not erroneous. Again the torso is checked to see if it is of reasonable size, and if the user is completely inside of the workspace. The head is also checked to see if it is of reasonable size. Lastly if the growing process cannot find the legs the routine fails. When any of these checks fail the routine waits for the next set of data and repeats the initialization phase.

A source of error in the autonomous routine emerges because the limb radii are not always measured. However, this does not cause any major problems to the tracking process. If the radii of the real person's limbs are larger than that of the model, the only change to the tracking process will be a slight decrease in efficiency. This is because when voxels are found within the body model they are assumed to be closest to that segment, and hence the distance to other segments is not measured. However if they are outside of the body model each voxel is projected onto all of the segments to determine which part it is closest too. If the limb radii are too small, a small number of voxels that would normally be inside of the model with be outside, and hence some extra computation is necessary. However, voxels still pull on the center axis of the corresponding limb, and therefore the resulting forces are identical in both cases. If the opposite is true (the model radii are larger than the actual radii) tracking accuracy will only be affected if a voxel that actually is closest to one segment is within the enlarged radii of another limb. This will only become an issue when limbs are close to one another. Accordingly there is a tradeoff between efficiency and accuracy when choosing the radii for autonomous initialization, but radii should be measured accurately if the subject may be performing movements where limbs come in contact with one another.

Another means to autonomously initialize the model is to save model parameters for each user and read them in as the user enters the workspace. The system uses voice communication, therefore it is easy to incorporate an option to simply tell the system your name while entering the workspace and skip the model estimation phase. However, the system must have an initial estimate of the pose. The autonomous model initialization routine can then be utilized, but only to estimate the pose. In this way the parameters that determine the size of each segment can be measured in any manner and read in from a file. This option is useful for applications where known subjects are being tracked by the system or where an exact model is required, in which case model parameters can be measured by hand and written to a file.

Figure 6:
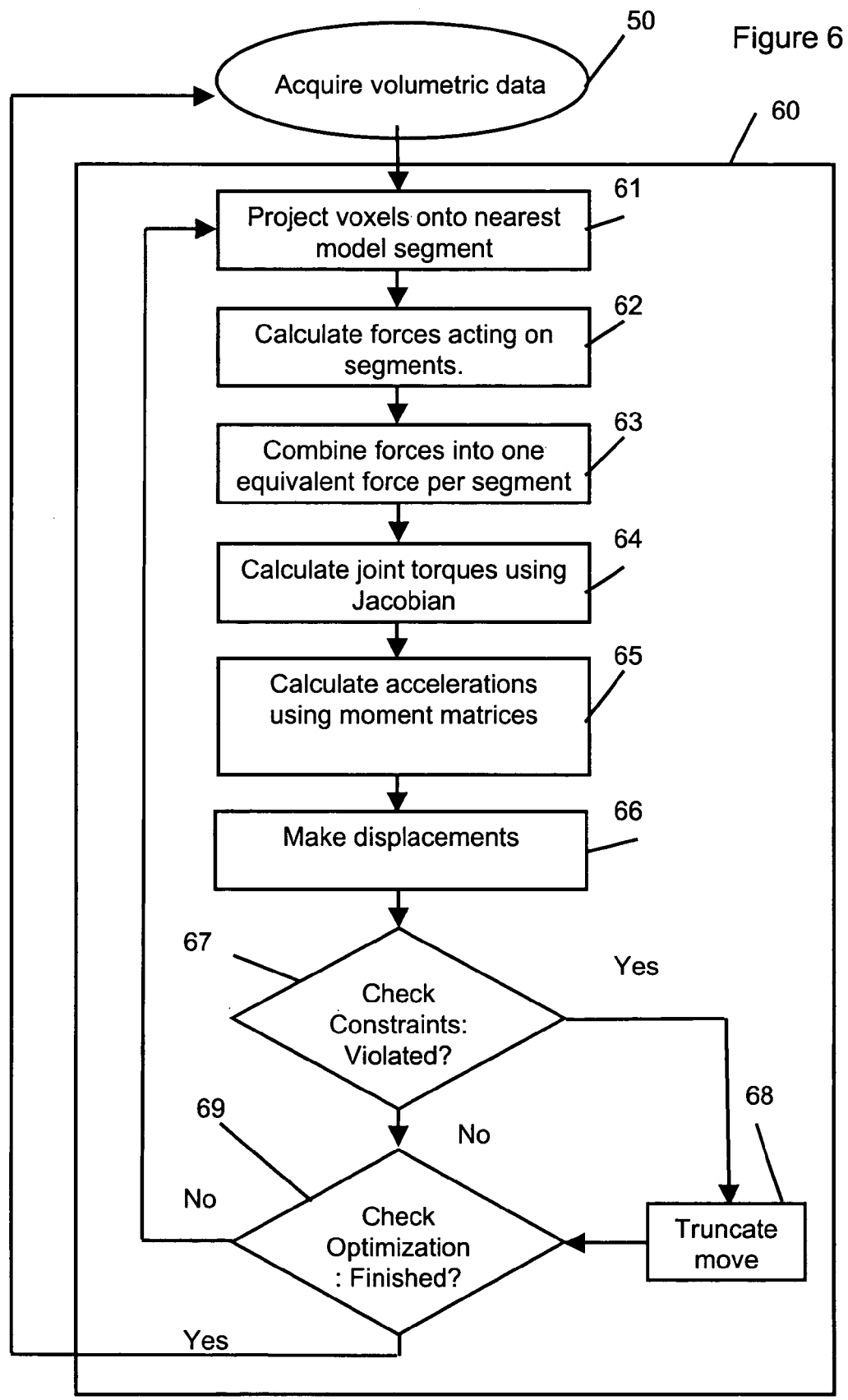
FIG. 6 Block Diagram of Alignment Method

Aligning the Model to the Data Set: Once the model has been initialized, tracking of the model can begin. Tracking the model is the process of aligning the model to subsequent data sets, collected on a frame by frame basis by the imaging system. FIG. 6 illustrates a block flow diagram summarizing the process of aligning the model to the data set. Tracking a subject within a workspace is accomplished by comparing the occupied voxels of each subsequent data set (frame) with the location of the model determined from the previous data set (frame). The tracking scheme is a physics based approach in which voxels from a subsequent data set exert forces on the model. Using this scheme an iterative optimization is used to align the model with the data, in which several small adjustments to the model's position and orientation are made for each new set of data.

Figure 7A:
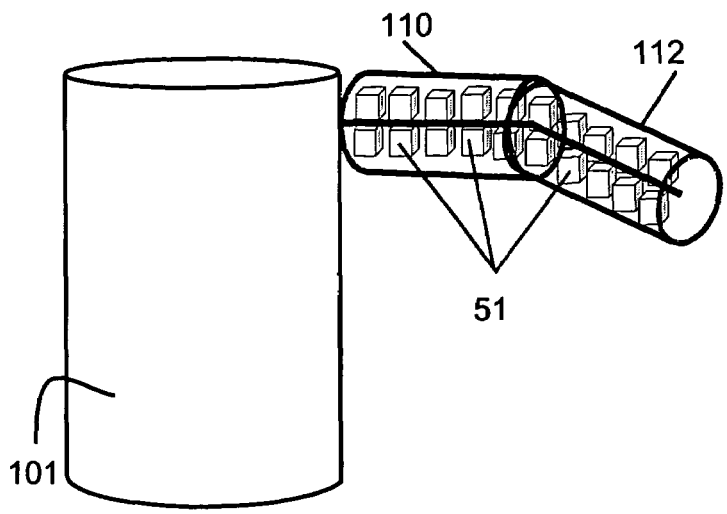
FIG. 7a Upper Limbs After Initialization
Figure 7B:
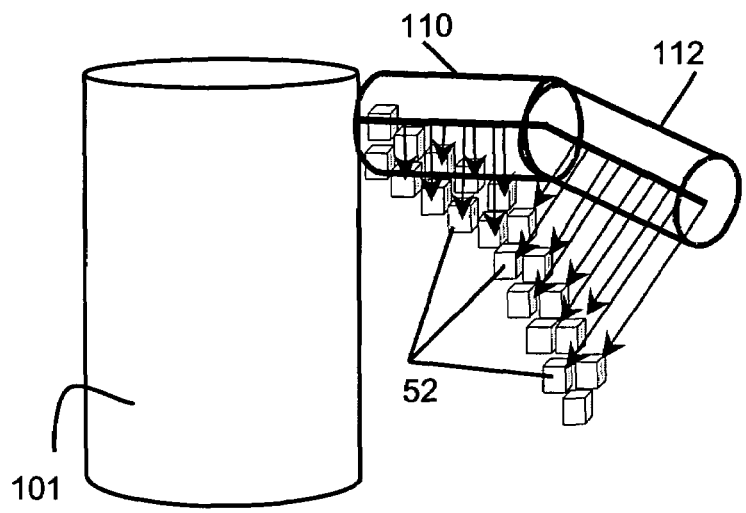
FIG. 7b Pulls Exerted by New Data Set On a Model
Figure 7C:
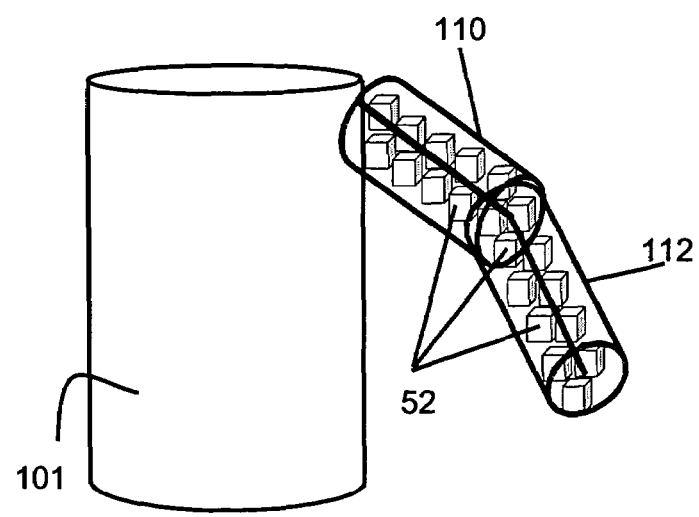
FIG. 7c Model After Alignment With the New Data Set

The model is designed so that only joint angles are required to determine the pose of succeeding segments, because the preceding segment in the chain anchors them. No anchor is used for the torso, which is the start of the chain. Force analysis of connected chains is widely known within the art for controlling the movement of robotic arms. As shown in FIGS. 7a through 7c, each voxel exerts a force upon the model, which act like springs to pull the model into alignment with the data.

For simplicity in FIGS. 7a through 7c only the torso (101) and limb segments (110) and (112) are shown to illustrate the method, but as will be seen the method is the same for all other limb segments of the model. FIG. 7a illustrates the model at the point initialization of the model is completed. Voxels (51) have been used to initialize, dimension and position, the models limb segments (110) and (112). FIG. 7b shows a new data set that has been collected from a subsequent video frame indicating a new set of voxels (52) are now occupied by the subject. The arrows represent the forces calculated by the method which will act to pull the model into alignment with the new data set. FIG. 7c illustrates the model after being aligned to the new data set. Aligning the model to each subsequent data set (image frame) is then repeated in a process of iterative optimization as described below.

The first step in the optimization is to calculate the pull each voxel (52) exerts on the model; hence the routine must project each voxel onto the model. The voxel is associated with the model segment that it is closest to, which is a valid assumption as long as the model does not move far between data sets. Since the operating speed is approximately 20 Hz, and a person does not move far in $1/20^{th}$ of a second, the assumption is applicable. The voxel is projected onto the center axis of the model segment it is nearest to. Hence each voxel pulls on the center axis of the segment that it is closest too, thereby pulling the model towards the voxel. The force exerted on the model is proportional to its distance from the model, and its calculation is described below.

The next step is to calculate an adjustment to the model due to the forces. Forces are transformed into accelerations acting on the model and the accelerations are then used to calculate adjustments via the principle that dist=at²/2, or $\vec{\theta} = \vec{\alpha} t^2/2$ for rotational accelerations. Time is arbitrary for the optimization since the forces and hence the accelerations are virtual. A time increment that gives a best guess for the size of the calculated adjustment is picked. Since the force applied is equal to the distance the model needs to move to align it with the data, if the time is set to 1 the size of the adjustment is appropriate. The method continues to iterate until the calculated adjustment falls below a threshold.

Projecting Voxels onto the Model: As illustrated in FIG. 7b, to project each voxel (52) onto the model, the process first estimates the distance from each segment to the voxel. The closest point on the torso (101) is estimated by rotating the voxel into the torso coordinate system, and then scaling the x and y axes so that the width and thickness of the torso are one, i.e. the torso model is now a cylinder of unit radius. In this coordinate system the closest point on the model, $\vec{C}$, to the voxel, $\vec{V}$, can be estimated as:

$$C_z = \begin{cases} V_z & \text{if } -h_t \le V_z \le h_t \\ h_t & \text{if } V_z > h_t \\ -h_t & \text{if } V_z < -h_t \end{cases},$$

$$(C_x, C_y) = \begin{cases} (V_x, V_y) & \text{if } \sqrt{V_x^2 + V_y^2} \le 1 \\ (V_x, V_y)/\sqrt{V_x^2 + V_y^2} & \text{if } \sqrt{V_x^2 + V_y^2} > 1 \end{cases}.$$

Where, $h_t$ is the height of the torso. The closest point on a limb (110-112) to a voxel is found using the same process except that the model is already a cylinder; hence $C_x = C_y$, and the length of the limb, l, is substituted for $h_t$. Since the head model is simply an ellipsoid, the closest point on the head model is $\vec{C} = \vec{V}/|\vec{V}|$. Then the point is simply transformed back into the desired coordinate system, and the distance between the voxel and the point is computed. The closest point on the entire model is found by simply calculating the distance to each segment and taking the smallest value. Forces are only applied to the body segment they are closest too, and work to pull the associated model point towards the voxel.

Force Calculations: Alignment forces act like springs to pull the model into alignment with the data; however unlike spring forces, the alignment forces correspond linearly with the distance between each voxel and the centerline of the segment nearest that voxel. This is done because the adjustment calculation is a linear estimate; hence the forces should correspond in a linear fashion. Accordingly forces are calculated as a vector extending from the model to the voxel. If the voxel is further than a threshold distance from the model, the voxel is considered to be erroneous and no force is produced (the threshold in the example embodiment is set to 6 in.). The pulls are aggregated to pull on the center axis of the model. Voxels nearest to the head or torso pull on the center of the head or torso. Voxels nearest to a limb pull on the point along the limb axis that is perpendicular to $\vec{C}$. This means that the optimization aligns the model as best it can to whatever data is present. If data is missing from a portion of a body segment, such as the upper portion of the arm, the optimization will align the center axis of that body segment with the remaining data.

Acceleration Calculation: In the optimization scheme, forces are used to compute virtual accelerations of the model, which are then used to calculate adjustments for the optimization. Translational accelerations are calculated using: $\vec{a} = \vec{f}/m$, where m is the mass of the segment. To compute the rotational accelerations, torques are first calculated about the joints using $\vec{\tau} = \vec{d} \times \vec{f}$. For the limbs the model is a system of connected segments; hence the Jacobian matrix, J, can be used to simplify torque calculations, $\vec{\tau} = J^T \cdot \vec{f}$. A Jacobian matrix is made up of the partial derivates of a system of equations. The Jacobian for a system of equations $$\begin{cases} y_1 = f_1(x_1, \ldots, x_n) \\ \vdots \\ y_m = f_m(X_1, \ldots, x_n) \end{cases} \text{ is } J = \begin{bmatrix} \frac{\partial y_1}{\partial x_1} & \cdots & \frac{\partial y_1}{\partial x_n} \\ \vdots & \ddots & \vdots \\ \frac{\partial y_m}{\partial x_1} & \cdots & \frac{\partial y_m}{\partial x_n} \end{bmatrix}.$$

Then under the principle that acceleration is equal to torque divided by inertia, Newton-Euler dynamics relates joint torques to the velocities and accelerations of a system:

$$\vec{\tau} = M(\theta)\vec{\theta}'' + \vec{v}(\theta,\theta') + \vec{g}(\theta).$$

M is the inertia matrix of the segments, $\vec{v}$ is a vector of the Coriolis and centrifugal terms, and $\vec{g}$ is a vector of gravity terms. However since the forces exist in a virtual environment and are simply trying to pull the model into alignment with the data, there are no Coriolis, centrifugal, or gravity forces. With this in mind the equations are simplified to directly relate the joint torques and the angular acceleration at each joint through the inertia matrix, $\vec{\alpha} = M^{-1}\vec{\tau}$.

The following sections demonstrate how the process of FIG. 6 is used to calculate adjustments, displacements, for each of the different model segments: the torso, head, and limbs, for the example of tracking a human form. It will be obvious to one skilled in the art that this method is generally applicable to tracking any form that can be modeled as rigid segments connected by flexible joints.

Torso Adjustment: The torso model used has six degrees of freedom: translation in three directions and three rotations. Accordingly, forces exerted on the torso must create both translational and rotational adjustments.

Translational accelerations are calculated according to $\vec{a} = \vec{f}/m$, where m is the mass of the torso and $\vec{f}$ is a force vector of the sum of all the forces exerted on the torso ($\vec{f} = \Sigma \vec{v} - \vec{c}$ where $\vec{v}$ is the center of the voxel and $\vec{c}$ is the center of the torso). The mass is set to the number of voxels that project onto the torso. Dividing $\vec{f}$ by the number of torso voxels sets $\vec{a}$ a to the average pull on the torso, which pulls the torso to the center of all the voxels that project onto the torso.

The rotational adjustment is calculated according to $\vec{\alpha} = M^{-1} \vec{\tau}$, where $\vec{\tau}$ is vector of the sum of the torques created by each force about the torso centroid, and M is the inertia matrix of the torso model. If these calculations are done in the torso coordinate system, M is a diagonal matrix of the moments of inertia for a cylindrical ellipse.

$$M = \begin{bmatrix} \frac{1}{12}m_t h_t^2 + \frac{1}{4}m_t t_t^2 & 0 & 0 \\ 0 & \frac{1}{12}m_t h_t^2 + \frac{1}{4}m_t w_t^2 & 0 \\ 0 & 0 & \frac{1}{8}m_t(w_t^2 + t_t^2) \end{bmatrix},$$

where $m_t$ is the mass of the torso and is set to the number of voxels projecting onto the torso, and $t_t$, $w_t$, $h_t$ are the thickness, width, and height of the torso. Torques are calculated using the fact that $\vec{\tau} = \vec{d} \times \vec{f}$. Because the force applied to the torso is equal to the distance from the origin, the equation $\vec{\tau} = \vec{C} \times \vec{V}$, where $\vec{C}$ is the location in the torso that is closest to the point and $\vec{V}$ is the point in torso coordinates, yields the torques about each of the axes. If the point is inside of the torso $\vec{C}$ is equal to $\vec{V}$. The torques are then applied to $\vec{\alpha} = M^{-1} \vec{\tau}$ to determine the angular accelerations.

However, for this optimization several of the torque terms caused by the voxel pulls do not make much sense in real-world application. Torque about z (spinning in a circle) is normally determined by voxels pulling from the front or behind the torso and voxels pulling on the left or right side of the torso, both pulling to twist the torso about z. The second term is unrealistic in that the torso is normally wider (shoulder to shoulder) than it is thick (front to back), and for an overweight subject the torso is round along z. In either case pulls from the side are not of much help to determine the twist about z. Hence only pulls in front or behind the torso are used to determine the rotation about z. A similar situation occurs for the rotations about x (front-to-back lean) and y (side-to-side lean). Forces in the z direction pertain to voxels above and below the torso, where the head and legs are located. Therefore this term is eliminated leaving the voxels in front and behind the torso to determine front-to-back lean and forces on the side to determine side-to-side lean. The remaining torques can now be applied to $\vec{\alpha} = M^{-1} \vec{\tau}$ to determine the angular accelerations.

The problem of missing data can still have a large effect on the optimization, and it is difficult to determine the orientation of the torso for an overweight subject whose torso may be close to round. To mitigate these problems the system includes some forces from the head and smalls regions of each limb. Forces that pull upward on the head are included to help center the torso along z. In addition forces that pull downward on the ends of the legs and arm (in the x direction of the lower limb) are transformed back into torso coordinates and also used to center the torso along z. Forces that pull on the upper third of the legs (nearest the hips) are transformed back into torso coordinates and used to both translate the torso along z and rotate it about x. Similarly forces that pull on the upper thirds of the arms (nearest the shoulders) are transformed back into torso coordinates and used to both translate the torso along z and rotate it about z and y. To minimize the effects of limb tracking errors on the alignment of the torso, forces from the lower two thirds of the limbs are not used to rotate the torso. In this way forces pulling on the end of the limbs and the head will still work to properly align the torso along its z axis, even if the subject is round (overweight) and it is hard to tell where the subjects torso stops and the legs begin or if missing data in the torso disrupts the alignment. Also points near the joints on the torso will work to align the torso rotationally, even when the subject is round or if points are missing from the torso.

Head Tracking: The head model is anchored to the torso, and hence only rotations need to be calculated. Rotations can be computed using the same equations: $\vec{\alpha} = M^{-1} \vec{\tau}$, where M is simply the diagonal inertia matrix of the ellipsoid used to model the head and $\vec{\tau}$ is the sum of the torques caused by each force applied to the head. Again the mass of the head, $m_h$, is set to the number of voxels that are closest to the head.

$$M = \begin{bmatrix} \frac{1}{5}m_h(h_h^2 + w_h^2) & 0 & 0 \\ 0 & \frac{1}{5}m_h(l_h^2 + h_h^2) & 0 \\ 0 & 0 & \frac{1}{5}m_h(l_h^2 + w_h^2) \end{bmatrix}$$

Torques are calculated about the base of the head. Pulls along z are again eliminated because of the noise due to the shoulders below the head. However for rotation about the z-axis of the head (axes are of the same initial orientation as the torso) both terms now apply.

Figure 8:
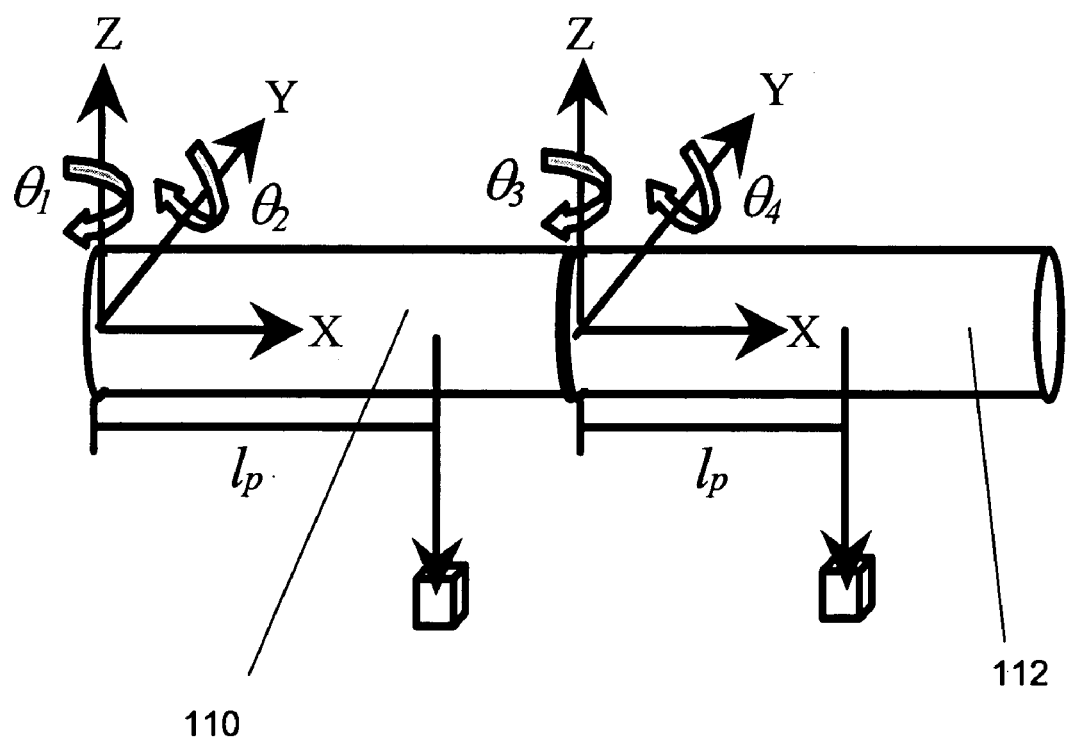
FIG. 8 Model Detail For Limbs

Limb Tracking: The model's limbs are also anchored at their respective joint locations on the torso, which are assumed to remain constant for a particular torso orientation. Therefore, the forces acting on the limbs translate to pure rotations in the form of torques. Since limbs are modeled as a system of connected segments as shown in FIG. 8, the Jacobian is used to simplify torque calculations, $\vec{\tau} = J^T \cdot \vec{f}$. In FIG. 8, only upper limb segments (110) and (112) are shown, but the process is the same for all limbs. The Jacobian for the two-link limb model used with two rotations at each joint is:

$$J^T = \begin{bmatrix} l_1 \sin(\theta_3)\cos(\theta_4) & l_1 \sin(\theta_3)\sin(\theta_4) & l_1 \cos(\theta_3) + l_p \cos(\theta_4) \\ l_1 \sin(\theta_4) & l_p \cos(\theta_3) + l_1 \cos(\theta_4) & l_p \sin(\theta_3)\sin(\theta_4) \\ 0 & 0 & l_p \\ 0 & l_p & 0 \end{bmatrix}.$$

Where $l_1$ is the length of the upper limb, $l_p$ is distance along the lower limb to the point the voxel projects onto, and $\vec{f}$ is in the lower limb coordinate system. If the voxels project onto the upper limb segment, torque is only produced about the upper joints:

$$J^T = \begin{bmatrix} 0 & 0 & l_p \\ 0 & l_p & 0 \end{bmatrix}.$$

Where $l_p$ is now the distance along the upper limb at which the voxel projects onto.

The torques are then summed and applied to $\vec{\alpha} = M^{-1}\vec{\tau}$ to determine the angular accelerations. However, because the model is a two-link system M is no longer a simple diagonal matrix. The symmetrical moment matrix for the rigid two-link system is:

$$M = \begin{bmatrix} M_{11} & M_{12} & M_{13} & M_{14} \\ M_{12} & M_{22} & M_{23} & M_{24} \\ M_{13} & M_{23} & M_{33} & 0 \\ M_{14} & M_{24} & 0 & M_{44} \end{bmatrix}.$$

$M_{11} = I_1 + \frac{1}{2}(I_2 + 2l_{1c}^2 m_1 + l_{2c}^2 m_2 + 2l_1^2 m_2 + 4l_{2c}l_1 m_2 \cos(\theta_3) \cos(\theta_4) + (I_2 l_{2c}^2 m_2) \cos(2\theta_4))$ $M_{12} = \frac{1}{2}(I_2 + l_{2c}^2 m_2)\sin(\theta_3)\sin(2\theta_4)$ $M_{13} = l_{2c}l_1 m_2 \cos(\theta_3) + (I_2 + l_{2c}^2 m_2)\cos(\theta_4)$ $M_{14} = l_{2c}l_1 m_2 \sin(\theta_3)\sin(\theta_4)$ $M_{22} = I_1 + l_{1c}^2 m_1 + (I_2 + l_{2c}^2 m_2)\cos(\theta_3)^2 + 2l_{2c}l_1 m_2 \cos(\theta_3)\cos(\theta_4) + \cos(\theta_4)^2 l_1^2 m_{2+}(l_1^2 m_2 + (I_2 + l_{2c}^2 m_2)\sin(\theta_3)^2)\sin(\theta_4)^2$ $M_{23} = (I_2 + l_{2c}^2 m_2)\sin(\theta_3)\sin(\theta_4)$ $M_{24} = (I_2 + l_{2c}^2 m_2)\cos(\theta_3) + l_{2c}l_1 m_2 \cos(\theta_4)$ $M_{33} = I_2 + l_{2c}^2 m_2$ $M_{44} = I_2 + l_{2c}^2 m_2$ Where $I_1 = m_1 l_1^2/3$, $I_2 = m_2 l_2/3$, and $l_{1c}$ and $l_{2c}$ are the lengths to the centers of segment 1 and segment 2. The masses of the limb segments ($m_1$ and $m_2$) are set to the number of voxels projected onto each of them.

Combining Forces: Since on each iteration of the optimization numerous voxels pull on a segment, it is far more efficient to combine all forces for each segment into a single force before applying the Jacobian and inverted inertia matrix. To ensure that the effects of the new force are equivalent to those of the original forces, the torques at the current joint and at all preceding joints must be remain constant. Accordingly these two equations must be observed:

$\Sigma \vec{f}_i l_i = \vec{F}\vec{L}, \Sigma \vec{f}_i(l_i + l_0 \cos(\theta)) = \vec{F}(\vec{L} + l_0 \cos(\theta)),$ where $\vec{F}$ and $\vec{L}$ are the unknowns. It can easily be shown that if the resultant force vector, $\vec{F}$, is equal to: $\vec{F} = \Sigma \vec{f}_i$, and if it acts on the axis of the arm at a distance equal to: $\vec{L} = \Sigma \vec{f}_i l_i / \Sigma \vec{f}_i$ from the joint, the torques at each joint will be equivalent to the original method. Hence, one can now replace the $\vec{l}_p$ in the Jacobian matrix with $\vec{L}$, and instead of applying the equations to each force one only need to apply them to the resultant force $\vec{F}$.

Dynamically Adjusting the Model to Comply with the Data: Invariance to missing data and/or occlusions is also built into the optimization by dynamically adjusting the model parameters to comply with the current data set. Since the volumetric data set can be noisy or have missing voxels, the tracking process must comply with the data. For instance when data is missing from a limb and only a few voxels project onto the limb, the optimization will still move the limb quickly to where the voxels lay. However if the weight of the limb is constant, the resulting adjustment will be too small because the weight of the segment is high in comparison to small number of voxels pulling on it. To avoid this problem the mass of each segment is dynamically set to the number of voxels that currently project onto the segment. In this way if only one voxel projects onto the segment the pull will still be large enough to align the segment with the data, and later if hundreds of voxels project onto the same segment its mass will again be set in proportion to the forces applied to it. Hence the pulls on the segment and the mass of the segment are dynamically linked so that they scale with one another.

A similar problem can occur with the center of mass of each segment when data is missing from one region of the limb. For instance if data is missing from the lower half of the lower arm and good data is still available on the upper half, torques computed on any preceding joints (i.e. the shoulder) will be skewed. This occurs because the center of mass of the segment is at the center of the segment, while all of the pulls are on the beginning of the segment. Hence while the pulls work to rotate the lower arm the center of mass wants to remain in its position. This causes the arm to rotate about its center of mass and shift the elbow, which erroneously adjusts the shoulder angles. To account for this potential problem the centers of mass of the segments are positioned at the center point of the voxels that project onto the segment. In this way the model approximates the data as closely as possible without changing its size or shape, and hence the adjustments generated are appropriate to align the model for any data set.

Figure 9A:
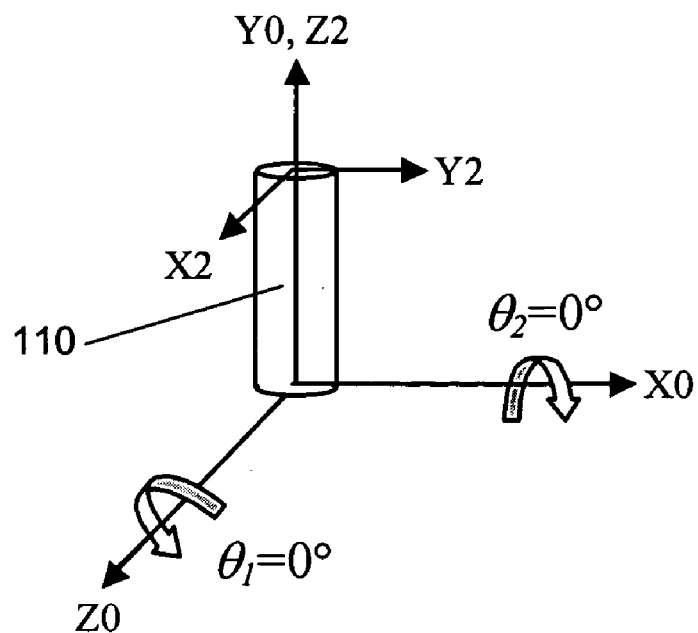
FIG. 9a Limb Orientation Without Jacobian Singularities
Figure 9B:
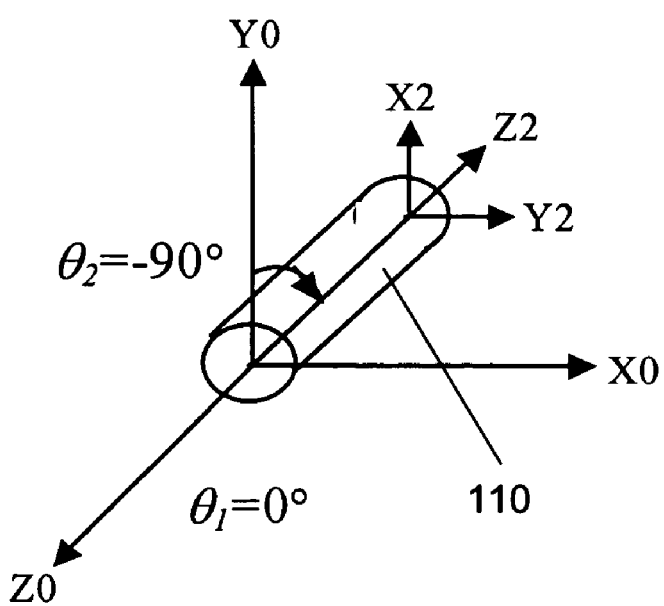
FIG. 9b Limb Orientation Causing Jacobian Singularities

Removing Singularities: Jacobian based schemes, can be problematic because of the existence of singularities. Jacobian based singularities appear because multiple degrees of freedom are modeled as a sequence of one-DOF joints with links of length zero between the joints. For example consider the two-DOF joint shown in FIGS. 9a and 9b. In FIG. 9a the joint is in a position where $\theta_1$ and $\theta_2$ are initially at 0°, if $\theta_2$ is rotated to −90° as shown in FIG. 9b, a force along Y2 will no longer create a torque. Hence a degree of freedom is lost and a singularity has been encountered.

To achieve robust tracking, any singularities in the model must be avoided; however, if any of the shoulder, elbow, hip, or knee joints are modeled as two one-DOF joints the above-mentioned singularity exists. Forces in the X2 or Y2 axes should produce a torques about X0 and Z0 independent of $\theta_1$ and $\theta_2$. A novel approach to removing the singularity is accomplished by rotating into a coordinate system where $\theta_1$ and $\theta_2$ are zero before the force is applied. Hence all singularities in a upper joint, a hip or shoulder, are eliminated.

Figure 10:
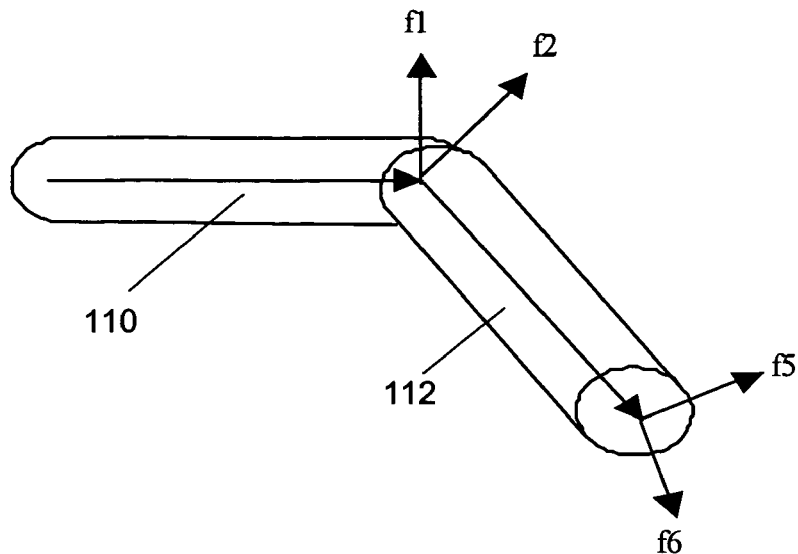
FIG. 10 Removing Singularities in The Jacobian

To remove singularities in the second joint, forces along the $f_5$ and $f_6$ axes as shown in FIG. 10 must also produce joint torques in the elbow or knee independently of the orientation of the lower limb segment; however the same singularity will occur as the magnitude of $\theta_4$, FIG. 8, approaches 90°. The problem is complicated because one cannot simply rotate into a coordinate system where $\theta_3$ and $\theta_4$, FIG. 8, are zero when there is a bend in the arm. To solve this problem the second joint is remodeled as four consecutive one-DOF joints instead of only two joints. The first two joint angles are set to account for the bend in the elbow or knee. The second two joint angles are always zero. Torques are only computed about the second two joints. Since all of the torques are now computed about joints whose angles are zero there are no singularities in the calculation. This mathematical trick moves the singularities to these first two joints; since torques are not computed across these joints the singularities do not have an effect. The inertia matrix, M, was consequently created for torques in the $f_1$, $f_2$, $f_5$, and $f_6$ directions, FIG. 10. Performing the calculations in this manner not only removes the singularities in the process but also decreases the complexity of the Jacobian and inertia matrices.

Additional Processing in the Alignment Process: After each iteration of the optimization, additional processing is performed to enforce joint limits, velocity constraints, collision constraints, and to perform recovery if tracking fails. All of these adjustments are made after each movement of the optimization process, so they do not affect the optimization process itself. They only correct the optimization when it moves to an illegal pose, makes an illegal move, or loses a segment. Hence, whenever the optimization moves out of the legal search space or makes an illegal move, the illegal part of the move is removed. In this way the optimization is allowed to align the model to the data as best it can while the post processing ensures the resulting pose is legal.

Joint Limits: Joint limit constraints are incorporated into the limb tracking to avoid moving into impossible poses because of erroneous data. Joint limits are fairly easy to set for an average human subject. However the model has two rotations in each limb at the upper joint and two at the lower joint, while an actual human limb has three rotations at each shoulder or hip and only one at the elbow or knee. Therefore, a correlation between the model and an actual human is needed before joint angle constraints can be established. The joint limits given in this section are rough estimates of a normal human's range of motion, but they are easily modified depending upon the application.

Figure 11:
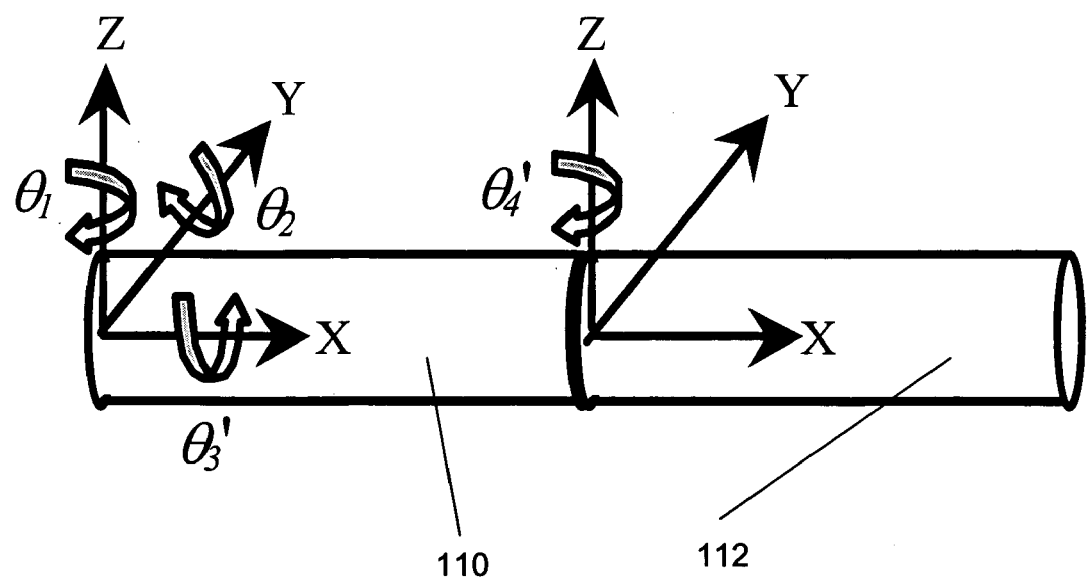
FIG. 11 Three and One Rotation Model

The relationships for the first two rotations (the upper joint angles) are fairly easy to compute. As shown in FIG. 11, $\theta_1$ simply indicates how far the limb (110-112) can rotate from the front to the back of the torso (not shown). $\theta_2$ allows the limb to rotate up and down from the first rotation, about the new y-axis of the limb. Accordingly joint limits for the upper arm are fairly easy to compute. However as the arm approaches vertical $\theta_1$ only determines which way the arm is tilting, and any value represents an achievable pose. With this in mind any value for $\theta_1$ is allowed when $\theta_2$ is greater than 75°. Table 2 lists the upper arm joint limits.

TABLE 2

Joint limit listings for the upper arms.

| Limb | Condition | Limit |
| --- | --- | --- |
| Right Arm | If $(abs(\theta_2) < 75°)$ | $-90° < \theta_1 < 135°$ |
| Left Arm | If $(abs(\theta_2) < 75°)$ | $\theta_1 < -90°$ or $\theta_1 > 45°$ |
| Right Arm | If $(abs(\theta_2) \geq 75°)$ | $-180° < \theta_1 < 180°$ |
| Left Arm | If $(abs(\theta_2) \geq 75°)$ | $-180° < \theta_1 < 180°$ |

Similar limits apply to the hips (see Table 3). It is easy to set the $\theta_1$ limit for the average human and assign a reasonable limit for $\theta_2$ according to the value of $\theta_1$. Again when the leg is pointed close to straight down any range of $\theta_1$ is acceptable, and for the legs this limit is set at 60°.

TABLE 3

Joint limit listing for the upper legs.

| Limb | Condition | Limit |
| --- | --- | --- |
| Right Leg | If $(\theta_2 < 60°)$ | $-135° < \theta_1 < 135°$ |
| Left Leg | If $(\theta_2 < 60°)$ | $\theta_1 < -45°$ or $\theta_1 > 45°$ |
| Right Leg | If $(\theta_2 \geq 60°)$ | $-180° < \theta_1 < 180°$ |
| Left Leg | If $(\theta_2 \geq 60°)$ | $-180° < \theta_1 < 180°$ |
| Right Leg | If $(\theta_1 > 0°)$ | $\theta_2 > -45°$ |
| Left Leg | If $(\theta_1 > 0°)$ | $\theta_2 > -45°$ |
| Right Leg | If $(\theta_1 \leq 0°)$ | $\theta_2 > 0°$ |
| Left Leg | If $(\theta_1 \leq 0°)$ | $\theta_2 > 0°$ |

When the optimization attempts to move past a joint limit the process simply moves the joint back into a legal formation. However the process must avoid hindering a legal rotation when enforcing joint limitations. That is if $\theta_1$ and $\theta_2$ both move by two degrees and $\theta_1$ moves out its legal range, $\theta_1$ is stopped at the limit while $\theta_2$ is allowed to continue to move. In most cases it is normally fairly obvious how to move back to a legal formation, but it can become complicated in situations such as when the limb is extended above or below the body ($abs(\theta_2)$ is near 90°). Accordingly correction conditions were added to ensure that moving out of an impossible pose still allows the optimization to move towards the proper alignment, as listed in Table 4 for the arms and Table 5 for the legs.

TABLE 4

Joint limit corrections for upper arms.

| Limb | Violation | Condition | Correction |
|---|---|---|---|
| Right Arm | If ($\theta_1 < -90°$ or $\theta_1 > 135°$) | abs($\theta_2$) < 65° | $\theta_1 = -90°$ or $\theta_1 = 135°$ |
| | | 65° < abs($\theta_2$) < 75° | abs($\theta_2$) = 75° |
| Left Arm | If ($-90° < \theta_1 < 45°$) | abs($\theta_2$) < 65° | $\theta_1 = -90°$ or $\theta_1 = 45°$ |
| | | 65° < abs($\theta_2$) < 75° | abs($\theta_2$) = 75° |

TABLE 5

Joint limit corrections for upper legs.

| Limb | Violation | Condition | Correction |
|---|---|---|---|
| Right Leg | If (abs($\theta_1$) > 135° and $\theta_2$ < 60°) | abs($\theta_1$) − 135° ≤ 60° − $\theta_2$ | abs($\theta_1$) = 135° |
| | | abs($\theta_1$) − 135° > 60° − $\theta_2$ | $\theta_2$ = 60° |
| Left Leg | If (abs($\theta_1$) < 45° and $\theta_2$ < 60°) | abs($\theta_1$) − 45° ≤ 60° − $\theta_2$ | abs($\theta_1$) = 45° |
| | | abs($\theta_1$) − 45° > 60° − $\theta_2$ | $\theta_2$ = 60° |
| Right Leg | If ($\theta_1 > 0$ and $\theta_2 < -45°$) | | $\theta_2 = -45°$ |
| Right Leg | If ($\theta_1 \leq 0$ and $\theta_2 < 0°$) | | $\theta_2 = 0°$ |
| Left Leg | If ($\theta_1 > 0$ and $\theta_2 < -45°$) | | $\theta_2 = -45°$ |
| Left Leg | If ($\theta_1 \leq 0$ and $\theta_2 < 0°$) | | $\theta_2 = 0°$ |

Resolving the correlation between the "two and two" DOF rotation system existing in the model and the "three and one" DOF orientation of an actual human is far more complicated in the lower arm. Therefore to set the joint limits for a lower arm, first rotate into the "three and one" orientation, make any correction due to a joint limit constraint, and then rotate back so the optimization can continue. FIG. 11 shows the joint configuration used for the "three and one" rotation model.

In the "three and one" configuration a rotation of $\theta_3'$ determines the twist in the shoulder, and $\theta_4'$ determines the bend in elbow. For the left arm $\theta_3'$ is set to rotate in the opposite direction as in the right arm; therefore a rotation of $\theta_3'$ will twist either arm in the same direction. Joint limits for the lower joint must be set so that the shoulder does not twist too far, and so that the elbow does not bend backwards or bend too far forward, as listed in Table 6.

TABLE 6

Joint limit listings for lower arms.

| Limb | Condition | Limit |
|---|---|---|
| Both Arms | If ($\theta_2 > 0°$) | $-90° < \theta_3' < 90°$ |
| Both Arms | If ($\theta_2 \leq 0°$) | $-90° - \theta_2 < \theta_3' < 90° - \theta_2$ |
| Both Arms | | $0° < \theta_4' < 150°$ |

Figure 12:
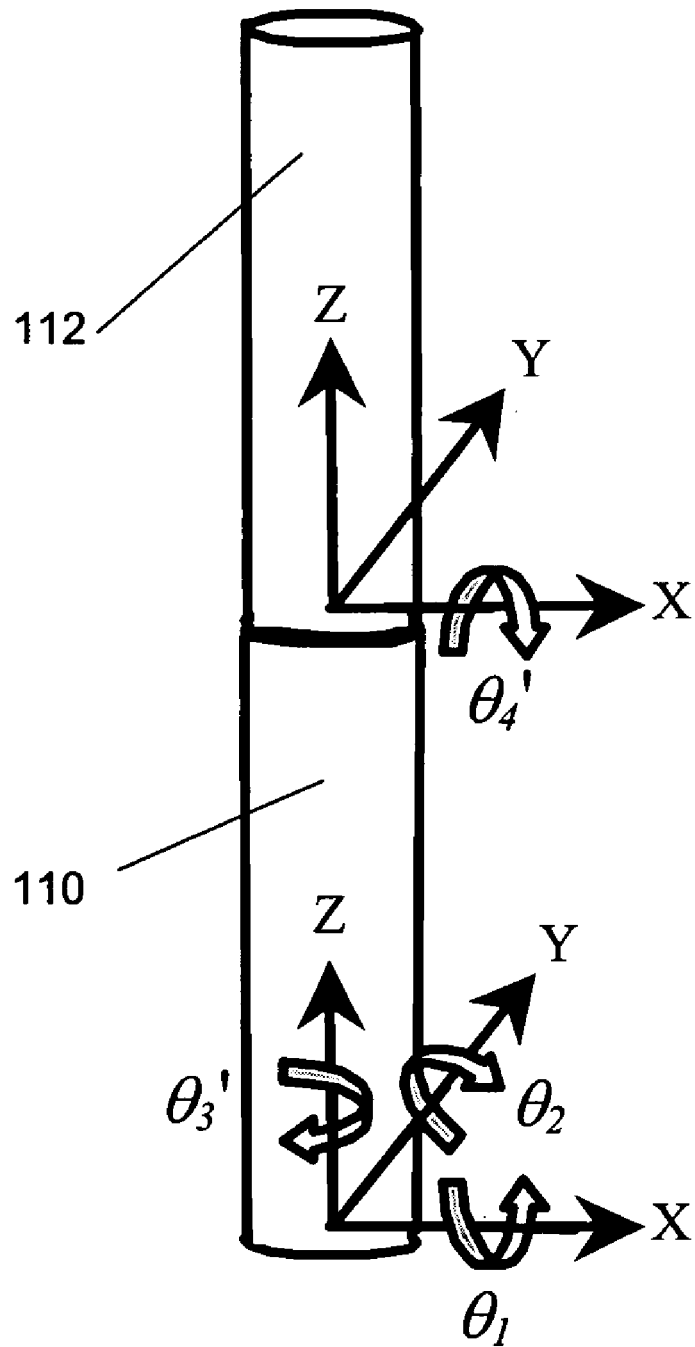
FIG. 12 Joint Limit Configuration For Nearly Vertical Upper Limbs

Another problem has to be considered when applying the joint limits to the model. If the upper arm is nearly parallel to the z-axis of the torso (i.e. straight up or down), $\theta_1$ can have any value and still be in a legal pose. However, the zero position of $\theta_3'$ shifts with $\theta_1$. To make the zero position of $\theta_3'$ known and constant, the zero position of the arm is modified to point straight overhead and the rotations $\theta_1$ and $\theta_2$ are changed to $\theta_1'$ and $\theta_2'$ when the limbs upper arm segment is near vertical. Hence when the arm nears vertical, abs($\theta_2$)>75°, the model is rotated into the new configuration as shown in FIG. 12. This new coordinate system is designed so that the same joint limits can be used; hence $\theta_3'$ and $\theta_4'$ can be interchanged with $\theta_3$ and $\theta_4$ in the tables herein.

Again when the joint limitations are broken the process must decide how to move back into a legal position without adversely effecting the optimization. For example in FIG. 8, if $\theta_3$ rotates too far it is not desirable to adjust $\theta_4$ to move back to a legal orientation. This is handled by inspecting the joint angles and computing the smallest move to bring the arm back into alignment. Corrections for the lower arm are listed in Table 7.

TABLE 7

Joint limit corrections for lower arms.

| Limb | Violation | Condition | Correction |
|---|---|---|---|
| Both Arms | If ($\theta_2 > 0°$ and $\theta_3 < -90°$) | $\theta_4 < -90° - \theta_3$ | $\theta_3 = 180° + \theta_3$ |
| | | $\theta_4 \geq -90° - \theta_3$ | $\theta_3 = -90°$ |
| Both Arms | If ($\theta_2 > 0°$ and $\theta_3 > 90°$) | $\theta_4 < \theta_3 - 90°$ | $\theta_3 = \theta_3 - 180°$ |
| | | $\theta_4 \geq -90° - \theta_3$ | $\theta_3 = 90°$ |
| Both Arms | If ($\theta_2 < 0°$ and $\theta_3 < -90° - \theta_2$) | $\theta_4 < -90° - \theta_2 - \theta_3$ | $\theta_3 = 180° + \theta_3$ |
| | | $\theta_4 \geq -90° - \theta_2 - \theta_3$ | $\theta_3 = -90° - \theta_2$ |
| Both Arms | If ($\theta_2 < 0°$ and $\theta_3 > 90° - \theta_2$) | $\theta_4 < \theta_3 - 90° + \theta_2$ | $\theta_3 = \theta_3 - 180°$ |
| | | $\theta_4 \geq \theta_3 - 90° + \theta_2$ | $\theta_3 = 90° - \theta_2$ |

A separate process was developed to set the joint limits for the leg. The leg limits must ensure that the knee does not bend backwards or too far, and also that the leg does not twist an unreasonable amount about the upper leg's main axis. If one assumes that the leg can twist 90° about the z-axis of the torso from the leg's zero position (the leg pointed straight down and kneecap facing forward along the y-axis of the torso), it is possible to create only one constraint to ensure the leg will not twist too far and that the knee will not bend backwards. This constraint simply states that the angle between the x-z plane of the torso and the foot is not smaller than angle between the same plane and the knee. To set this limit angles are computed in torso coordinates according to:

if ($z_{foot} > z_{knee}$)

Figure 13:
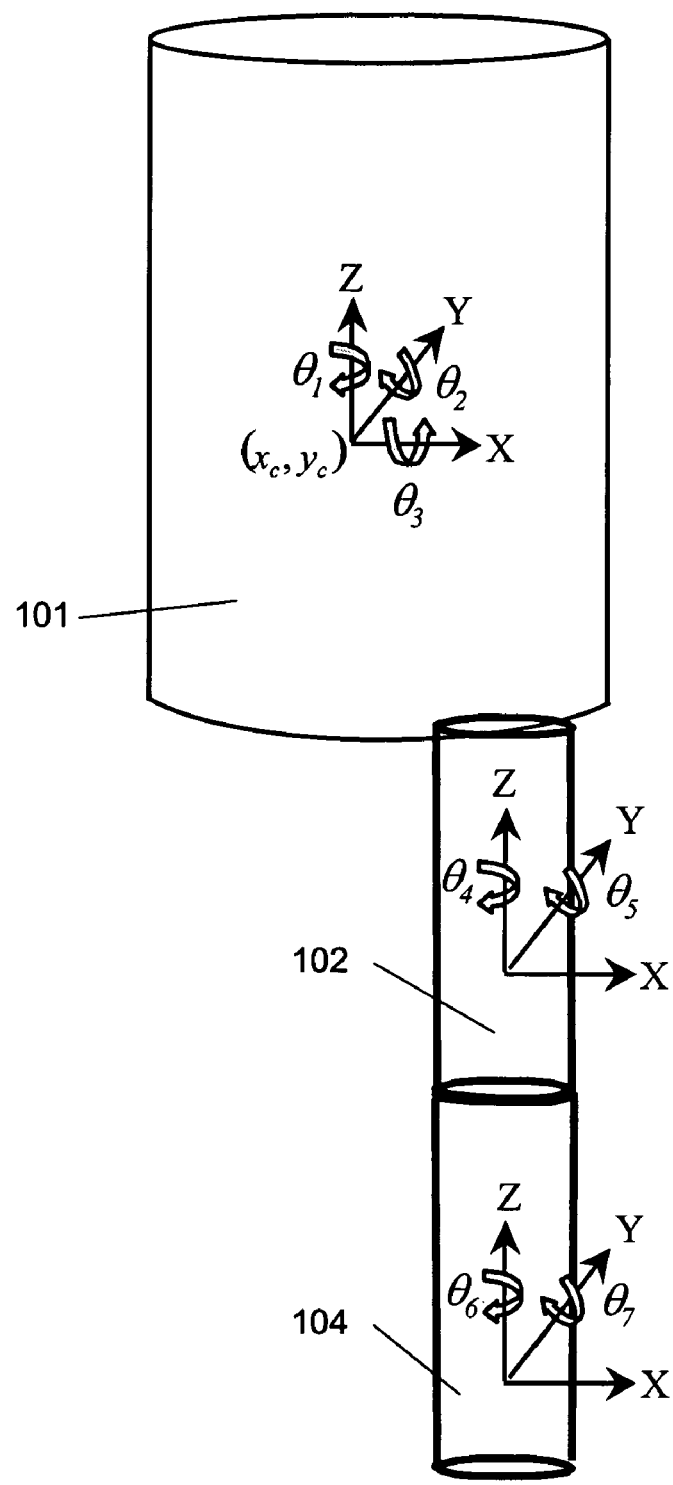
FIG. 13 Joint Limit Configuration For Lower Limbs

$\theta_u = a\tan 2(y_{knee}, \sqrt{x_{knee}^2 + z_{knee}^2})$ $\theta_L = a\tan 2(y_{foot}, \sqrt{x_{foot}^2 + z_{foot}^2})$ else $\theta_u = a\tan 2(y_{knee}, -\sqrt{x_{knee}^2 + z_{knee}^2})$ $\theta_L = a\tan 2(y_{foot}, -\sqrt{x_{foot}^2 + z_{foot}^2})$.

Where $\theta_u$ is the angle between the x-z plane of the torso and the knee and $\theta_L$ is the angle between the x-z plane and the foot. The coordinates are illustrated in FIG. 13.

Ensuring that the leg does not bend too far forward is easily accomplished by setting a limit for the angle between the upper and lower leg segments. This angle is computed in upper leg coordinates according to: $\theta_5 = a\tan 2(-x_{foot}, l_2)$. Table 8 shows the limits for these new lower leg angles.

TABLE 8

Joint limit listings for lower legs.

| Limb | Limit |
|---|---|
| Both Legs | $\theta_L \geq \theta_u$ |
| Both Legs | $\theta_5 > 45°$ or $\theta_5 < 0°$ |

The corrections when these limits are broken are straightforward. For the normal range of motion there is no feasible region in which both constraints are broken and adjustment of only one angle will correct both of them. Therefore, one can simply adjust whichever constraint is broken, as listed in Table 9.

TABLE 9

Joint limit corrections for lower legs.

| Limb | Violation | Correction |
|---|---|---|
| Both Legs | $\theta_L < \theta_U$ | $\theta_L = \theta_U$ |
| Both Legs | $0° < \theta_5 < 45°$ | $\theta_5 = 0°$ or $\theta_5 = 45°$ |

Velocity Constraints: Velocity constraints ensure that joints are not rotating faster than is reasonable for an average human, and that the body is not translating at an unreasonable rate. Movement of the limbs can be measured either by the distance their endpoints travel or by the change in joint angles. The distance the endpoint of a limb moves is not the best measure of velocity because it does not take into account the length of a limb. The longer a limb is the more its endpoint should be allowed to move. The change in joint angles is a more direct measure of how fast a limb is moving; however in some configurations a large change in joint angle does not necessarily cause the limb to move very far. For instance when the arm is aligned with the z-axis of the torso a large change in $\theta_1$ has very little effect on the position of the elbow. Therefore a single angle is computed between the position of the limb prior to the current data set and the limbs current position. This angle gives a direct measure of how quickly a limb is moving.

The angle is simply the angle between the position of the joint in previous data set, $\vec{P}_s$, and its current position, $\vec{P}_c$, in torso coordinates, and is calculated as: $\theta = \sin^{-1}(\sqrt{(\vec{P}_c - \vec{P}_s)^2}/d)$, where d is the distance from the hip or shoulder to the joint center. If the limit is being imposed on an upper limb, d is simply the length of that limb. If the angle is greater than a set upper limit, the move is truncated. When the move is truncated, the process simply draws a straight line between the previous location of the joint and its current location, and moves the joint to the point on the line at the limit. Therefore the joint is positioned at the point on the segment $\vec{P}_c = \vec{P}_s$ that is $d*\sin(V_L)$ from the stored position, where $V_L$ is the velocity limit. $V_L$ in the example embodiment is set to 10°, which allows a joint to rotate approximately 180° in a second.

The velocity limit for translation of the body is typically set high. This is because there must be as much erroneous data as there is good data to pull the torso away from the good data. With that amount of erroneous data all tracking will probably fail. In one embodiment of the invention the limit is set so that the torso cannot move faster than 10 meters in a second, but a situation where the limit has aided tracking has yet been observed.

Collision Constraints: In this tracking method a collision occurs when the optimization moves two segments so that they partially overlap one another. When an overlap occurs the optimization process moves back a step and attempts to remove the portion of the move that caused the overlap. Accordingly collision constraints are performed after each iteration of the process. This method allows the optimization to function as normally as possible, while removing any portion of a move that overlaps two segments. The process also remains efficient with this type of collision avoidance because the correction process does not require voxels to be re-projected onto the model, which consumes the vast majority of processing time. The only problem is that because the correction is an estimate, a tiny overlap may still occur. However, in comparison to the accuracy of both the model and the tracking results the small error in this correction is trivial.

To simplify the process, collisions have been broken up into several different categories: a collision of an upper limb segment with the torso, a collision of a lower limb segment with the torso, and a collision between limb segments. Joint limits prevent the legs from moving inside of the torso; therefore only arms are checked to see if a collision with the torso has taken place. Detecting an overlap of two segments is fairly straightforward and well known to those skilled in the art. Hence discussion of the process to detect an overlap is not included herein, but it is mentioned that the routines return the points on each segment that are closest to the axes of the other segment, $(x_a, y_a, z_a)$ and $(x_b, y_b, z_b)$.

When an overlap is found the process first re-computes the moves for each limb involved in the collision using an unlinked model. In other words each segment of the limb is optimized separately. This is done to stop erroneous or misassigned voxels that are pulling on one segment of the limb from affecting the pose of the entire limb. In this way if erroneous or misassigned voxels are pulling on the lower limb, the pose of the upper limb will still be correct. Re-computing the moves separately is accomplished by first adjusting the upper limb segment according to only the pulls on the upper limb. For every segment a single force, $\vec{F}$, has already been computed, and a corresponding model point at which the force pulls, $\vec{L}$, that is equivalent to all the pulls applied to that limb segment (see "combining forces" above). First the limb is moved back to its position before the last move. Then the move is recalculated by simply applying the stored force, $\vec{F}$, to the Jacobian and inertia matrices a single segment:

$$J = \begin{bmatrix} 0 & 0 & L[2] \\ 0 & L[1] & 0 \end{bmatrix} \text{ and } M = \begin{bmatrix} ml^2/3.0 & 0 \\ 0 & ml^2/3.0 \end{bmatrix},$$

where m is the mass of the limb segment, and l is the length of the limb segment. The procedure is repeated for the lower limb. Now the moves of each limb segment are independent of any erroneous pulls that may be exerted on a connecting segment. Once the move has been recalculated for each limb involved in the collision, the process rechecks to see if the collision is still present.

A collision occurs because either erroneous voxels have pulled one segment until it overlaps with another, or because voxels that should be associated with one segment erroneously pull another segment into collision with the first segment. If a limb collides with the torso only the pose of the limb is adjusted. The pose of the torso is assumed to be correct, because even if some erroneous voxels are assigned to the torso or if some of the limbs voxels are misassigned to the torso, they will have little effect on the much larger torso segment. In this case the arm is simply moved away from the torso. If two limbs are overlapped both limbs are adjusted to remove the overlap. Accordingly, the discussion will start with the easiest collision to correct, a collision between an upper limb segment and the torso, and then examine a collision of the lower limb with the torso, and lastly a collision between two limb segments.

Upper Limb Collision with the Torso: When an elbow moves inside of the torso the process can simply move it back out. The only way the upper arm can be inside of the torso is when $\theta_2$ in FIG. 8 is set so that the limb is rotated down too far; therefore, one can simply adjust $\theta_2$ so that the limb is outside of the torso. Accordingly the routine first transforms $x_{elbow}$ and $y_{elbow}$ to torso coordinates:

$x_{elbow} = \cos(\theta_1)\cos(\theta_2)$ and $y_{elbow} = \sin(\theta_1)\cos(\theta_2)$.

Then it adjusts $\theta_2$ so that the point $(x_{elbow}, y_{elbow})$ is the radius of the elbow, $r_1$, outside of the torso: $x_{elbow} = (l_b + r_1)\cos(\theta_1)$ and $y_{elbow} = (w_b + r_1)\sin(\theta_1)$, while $\theta_1$ is left unchanged. The optimization is allowed to find the optimum value for $\theta_1$, while $\theta_2$ is set to hold the arm from overlapping with the torso. However when the upper arm is moved to the new position it alters the orientation of the lower arm. To account for this whenever a correction is made to an upper limb segment because of a collision, the lower limb segment is adjusted so that the hand or foot is as close as possible to its position prior to the change. The process also transforms the forces that are pulling on the lower limb to account for its new orientation. This precaution is taken in case the lower limb is also colliding with a segment and must be adjusted.

Lower Limb Collision with the Torso: When an overlap occurs between a lower arm segment and the torso, the lower arm is returned to its orientation before the move and the upper arm is left in its new position. However because the upper arm has moved, the lower arm may be overlapped with the torso. If this is true the lower arm is moved outside the torso, so that the angle to the overlap point, $\theta = \operatorname{atan}(y_a/x_a)$, remains constant (where $(x_a, y_a, z_a)$ is the point on the limb closest to the torso and $(x_b, y_b, z_b)$ is the point on the torso closest to the limb). The point just outside of the torso can be estimated in the transformed coordinate system: $(x_a, y_a) = (x_d/d, y_d/d)$, where $$d = \frac{\sqrt{x_a^2 + y_a^2}}{1.0 + r_l / \left( \sqrt{w_t^2\cos(\theta)^2 + t_t^2\sin(\theta)^2} \right)}.$$

In the equation: $r_l$ is the radius of the limb, and $w_t$ and $t_t$ are the width the thickness of the torso. The process then transforms the point back into upper arm coordinates and recalculates the angles for the lower arm.

If the arm was not already overlapped a portion of the move is used to progress to the collision point. Using a linear approximation the portion of the move needed to get to the collision point is equal to $$P_m = \frac{Dis_{BeforeMove} - Dis_{AtCollisionPt}}{Dis_{BeforeMove} - Dis_{AfterMove}},$$

which will move the limb very close to the collision point. If the adjustment of the upper arm by itself had already caused an overlap $P_m$ is set to zero, because the limb is already at the collision point.

Once the limb is at the collision point, the process removes the portion of the remainder of the move that causes an overlap and finishes the move. This is done by taking the remainder of the force projected onto the arm segment, $\vec{F}_r = \vec{F}(1.0 - P_m)$, and removing the portion that pulls in the direction of the collision. The portion of the force pulling in the collision direction is easy to find. The vector between the collision points, $\vec{C}_d = (x_a - x_b, y_a - y_b, z_a - z_b)$, is oriented in the collision direction. The portion of the force in the collision direction is equal to the dot product of the normalized collision vector, $\hat{C}_d$, and the force vector, $\vec{F}_r$, or simply: $\vec{F}_c = \vec{F}_r / |\vec{F}_r| (\vec{F}_r \cdot \hat{C}_d)$. The final force, $\vec{F}_f = \vec{F}_r - \vec{F}_c$, is then applied to the torque and acceleration equations for only the lower limb segment to calculate the final adjustment.

Limb Collision with another Limb: When an overlap occurs between two limb segments, the limb segments are returned to their orientation before the move. Once again if one or more of the limb segments is a lower limb, the movement of the upper limb could cause the lower limb to already be overlapped. If an overlap occurs in this position, the limb must be moved away from the collision. In this case each limb is simply moved half the amount of the overlap away from the collision. Hence $(x_a, y_a, z_a)$ is moved a distance of $0.5(d_p - (r_a + r_b))$ in the direction defined by $(x_a - x_b, y_a - y_b, z_a - z_b)$, and $(x_b, y_b, z_b)$ is moved $0.5(d_p - (r_a + r_b))$ in the opposite direction. Then the angles for the joint segments involved in the collision are set to the new positions.

The process then checks to determine how much each limb movement contributed to the collision. This is done by comparing the current distance between the closest points on the limbs, $d_p$, the distance between the points with both moves made, $d_{ab}$, and the distance between the points with each of the moves made, $d_a, d_b$. The percentage that each limb-segment move contributed to the overall collision is calculated according to: $p_{a/b} = (d_p - d_{a/b})/(d_p - d_{ab})$ If either $d_a$ or $d_b$ is greater than $d_p$, the move of that arm segment is actually away from the collision. Hence $p_{a/b}$ for that segment is set to 0 and the entire move for that segment is executed, otherwise the calculated $p_{a/b}$ determines how much the move contributed to the collision.

It is noted that if the collision occurs very close to the preceding joint even a very small move will result in a large change in the joint angles and hence orientation of the limb. Therefore if the collision point is close to the joint for limb-segment a, the ratio needs to be changed so that limb-segment b is moved enough to remove the current overlap, and vice-versa. In this case $p_a$ is set to 0, and $p_b$ is set to 1. If the collision happens to occur very close to the joints of both limb-segments, then the upper limb-segments are adjusted to move out of the collision, and $p_a$ and $p_b$ are set to 0 (note that it is impossible for a collision to occur next to the joints of two upper limb segments, hip and shoulders).

As before, the next step is to move to the collision point, if the points were already overlapped the limbs should already be positioned at the collision point. Otherwise the move is assumed to be linear, and the portion of the moves needed to get to the collision point is calculated according to:

$$P_m = \frac{Dis_{BeforeMove} - Dis_{AtCollisionPt}}{Dis_{BeforeMove} - Dis_{AfterMove}}.$$

Using this approximation each limb is moved a fraction of the total move, limb a is moved the percentage $p_a * P_m$ of its total move and limb b is moved $p_b * P_m$ percent of its total move. This linear approximation moves the limbs very close to their collision point.

Once at the collision point, the move is finished yet again with the portion of the move causing the overlap removed. As before this is done by taking the remainder of the force projected onto the arm segment, $\vec{F}_r = \vec{F}(1.0 - P_m)$, and removing the portion that pulls in the direction of the collision. The portion of the force pulling in the collision direction is easy to find. The vector between the collision points, $\vec{C}_d = (x_a - x_b, y_a - y_b, z_a - z_b)$, is oriented in the collision direction. The portion of the force in the collision direction is equal to the dot product of the normalized collision vector, $\vec{C}_d$, and the force vector, $\vec{F}_r$, or simply: $\vec{F}_c = \vec{F}_r (\vec{F}_r \cdot \vec{C}_d)$. The final force, $\vec{F}_f = \vec{F}_r - \vec{F}_c$, is then entered into the Jacobian, $\vec{\tau} = J^T \cdot \vec{F}_f$, and Inertia equations, $\vec{\alpha} = M^{-1} \vec{\tau}$, for the limb segment to calculate the final adjustment.

Error Recovery: The method includes a recovery process in case it "loses" a limb. After each iteration the recovery process checks whether too few voxels are close to each of the arms. When $n_{voxels} < (l_1 + l_2)/l_{voxel}$ for a limb the routine assumes the limb is lost and attempts to grow the limb instead.

When a limb is lost the shoulder and hip locations are still known from the torso tracking. Therefore, as in the initialization routine, a growing process is started from the corresponding joint location on the torso. The process slowly moves out the limb, and as a result the last point found should correspond to the extent of the limb, for example the hand or foot. New limb angles are calculated with the elbow or knee straight and the limb directed at the last point found. The optimization then continues to refine the pose from this estimate; hence if the limb is bent the optimization will bend the limb into alignment with the data.

Growing can fail if there are no points on the limb, if gaps in the points are larger than the distance threshold, or if the torso pose is erroneous and the growing process is started from the wrong position. In an embodiment of the invention, failure is assumed when the growing process finds fewer than enough voxels to fill 50% of the limb model volume. When growing fails the process simply leaves the limb where it was last located and waits for the next set of volumetric data.

Growing also has problems if limbs are touching one another. To mitigate the problem the growing process is limited so that it can only include points on the corresponding side of the body. Accordingly if the limb is extended across the torso the process will stop growing at the point on the limb that passes the center of the torso (crossing the y-z plane of the torso). In most cases the optimization is still able to recover from this point. However if both legs are crossed or a similar scenario occurs the optimization may not be able to determine which voxels belong to which limb and can fail.

Growing also has a difficult time finding the limb when it lies next to the torso. The data used in tracking can be noisy and the visual hull can be inexact near the torso. Therefore it is possible that the data may be not accurate enough to detect a limb's exact pose when it lies next to the torso. If growing is attempted it moves randomly around "noise" voxels near the surface of the torso. Hence a threshold is set to determine how far from the torso a point must be to be considered from growing, $2.0 * l_{voxel}$. Problems will not occur when only a portion of the limb comes in contact with the torso because there is still enough separation on the rest of the limb to distinguish between the rest of the limb and the torso.

Recovering the pose of the torso when the process is reporting an erroneous torso pose is an extremely difficult problem when only volumetric voxel data is available. Since the torso is always pulled towards the center of the voxels, the number of voxels that project onto the torso is not a good indicator of when the torso has been lost. In practice the process normally returns to the appropriate pose once good torso data reappears in subsequent frames.

Additional objects, advantages and novel features of the invention will become apparent to those skilled in the art upon examination of the description or may be learned by practice of the invention. The objects and advantages of the invention may be realized and attained as particularly pointed out in the appended claims. It is intended that the scope of the invention be defined by the appended claims.

What is claimed is:

1. A Markerless method for tracking a subject in a workspace comprising:
    providing a video imaging system comprising:
        a plurality of video cameras simultaneously viewing the subject in said workspace;
        means for digitally acquiring images output from said video cameras; and,
        means for digitally processing said images;
    calibrating said video cameras and said workspace, said workspace further comprising a three dimensional array of voxels;
    providing a model template for said subject comprising a plurality of rigid segments linked by joints;
    initializing a model of said subject comprising:
        acquiring a first volumetric data set from said video imaging system;
            said first volumetric data set comprising a listing of said voxels occupied by said subject;
            dimensioning the rigid segments of the model template by fitting said rigid segments to said first volumetric data set;
    acquiring a second volumetric data set from said video imaging system, said second volumetric data set further comprising listing of said voxels occupied by said subject;
    aligning the model to said second volumetric data set, said aligning further comprising calculating in three dimensions a plurality of forces acting on said model, applying said plurality of forces to said model, said plurality of forces causing a displacement of the model;
        wherein aligning said model to said second volumetric data set further comprises:
            (a) projecting said occupied voxels from said second data set onto said rigid segments of the model, wherein each of said occupied voxels is projected onto each of the rigid segments nearest each of said occupied voxels;
            (b) calculating a force exerted on each of said rigid segments by each of said occupied voxels projected onto each of said rigid segments;
            (c) combining the force exerted on each of said rigid segments into an equivalent force exerted on each of said rigid segments;
            (d) calculating a torque exerted on each of said rigid segments, about each of said joints;
            (e) calculating a translational acceleration resultant from said equivalent force, acting on each of said rigid segments;
            (f) calculating a rotational acceleration resultant from said torque, exerted on each of said rigid segments, about each of said joints;
            (g) determining an incremental displacement of each of said rigid segments resulting from the calculated accelerations;
            (h) displacing each rigid segment by the calculated incremental displacement;
            (i) computing a distance between each of said occupied voxels and each of said rigid segments each of said occupied voxels is projected onto;
            (j) comparing the computed distance to a threshold value; and
            (k) repeating steps (b) through (j) until said computed distance is less than the threshold value;
                whereby said model segments are iteratively aligned to the second data set; and,
    repeating the steps of acquiring a second volumetric data set and aligning the model to said second volumetric data set ad infinitum.

2. The method of claim 1 wherein calculating a force on each of said rigid segments further comprises:
    providing said model of said subject further comprising:
        a first segment;
        a second segment having a first end and an opposed second end, said first end of said second segment joined to said first segment by a first rotatable joint;
        a third segment having a third end and an opposed fourth end, said third end of said third segment joined to said second end of said second segment by a second rotatable joint, said first, second and third segments being rigid segments;
        a first joint model of said first rotatable joint, said first joint model further comprising two joint elements, each of said two joint elements having one degree of freedom and an included angle;
        a second joint model of said second rotatable joint said second joint model further comprising four joint elements, each of said four joint elements having one degree of freedom and an included angle;
    performing a coordinate transformation of said second segment, wherein said included angle of said two joint elements of said first joint model is equal to zero;
    applying a Jacobian to calculate said force exerted on said second segment by each of said occupied voxels projected onto said second segment;
    selecting two of said four joint elements comprising said second joint model, setting said included angle of the two selected joint elements in said second joint model to zero;
    applying a Jacobian to calculate said force exerted on said third segment by each of said occupied voxels projected onto said third segment;
        whereby singularities are avoided in the Jacobian calculations.

* * * * *